(12) United States Patent
Achmann et al.

(10) Patent No.: US 10,806,387 B2
(45) Date of Patent: Oct. 20, 2020

(54) MEDICAL DEVICE AND METHOD FOR MANUFACTURING A MEDICAL DEVICE

(71) Applicant: Roche Diabetes Care, Inc., Indianapolis, IN (US)

(72) Inventors: Sabine Achmann, Mannheim (DE); Marcel Thiele, Mannheim (DE); Sebastian Pankalla, Ludwigshafen (DE); Jonathan Seidel, Limburgerhof (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/562,949

(22) Filed: Sep. 6, 2019

(65) Prior Publication Data
US 2019/0388013 A1 Dec. 26, 2019

Related U.S. Application Data

(63) Continuation of application No. PCT/EP2018/057007, filed on Mar. 20, 2018.

(30) Foreign Application Priority Data

Mar. 21, 2017 (EP) .................................. 17161991

(51) Int. Cl.
*H01R 12/00* (2006.01)
*A61B 5/1468* (2006.01)
(Continued)

(52) U.S. Cl.
CPC ........ *A61B 5/1468* (2013.01); *A61B 5/14532* (2013.01); *G01N 27/3272* (2013.01); *C12Q 1/006* (2013.01)

(58) Field of Classification Search
CPC .............. A61B 5/1468; A61B 5/14532; A61B 2562/12; A61B 2562/166; A61B 5/6848;
(Continued)

(56) References Cited

U.S. PATENT DOCUMENTS

| 5,413,690 A | 5/1995 | Kost et al. |
| 5,762,770 A | 6/1998 | Pritchard et al. |

(Continued)

FOREIGN PATENT DOCUMENTS

| CN | 104799866 A | 7/2015 |
| EP | 1 152 239 A1 | 11/2001 |

(Continued)

OTHER PUBLICATIONS

International Search Report and Written Opinion of the International Searching Authority, PCT/EP2018/057007, dated Jun. 18, 2018; 16 pages.

*Primary Examiner* — Abdullah A Riyami
*Assistant Examiner* — Nelson R. Burgos-Guntin
(74) *Attorney, Agent, or Firm* — Bose McKinney & Evans LLP

(57) ABSTRACT

A medical device and method of making the medical device are disclosed. The medical device includes a sensor having an interconnect. The interconnect has a first conductive layer, an insulation layer, and a second conductive layer separated from the first conductive layer by the insulation layer. An electrical contact is provided that is electrically connected to the second conductive layer and is contactable from the side of the interconnect that opposes the second conductive layer. The electrical contact is provided free of micro-vias. The medical device also includes an electronics assembly having an electrical connector, the electronics assembly configured to mate with the interconnect to estab-
(Continued)

lish an electrical connection between the electrical connector and the first conductive layer via the electrical contact.

20 Claims, 4 Drawing Sheets

(51) Int. Cl.
*A61B 5/145* (2006.01)
*G01N 27/327* (2006.01)
*C12Q 1/00* (2006.01)

(58) Field of Classification Search
CPC .. A61B 5/6867; G01N 27/3272; C12Q 1/006; H05K 3/4015; H05K 3/403; H05K 3/12; H05K 2201/10151
USPC .......................................................... 439/55
See application file for complete search history.

(56) References Cited

U.S. PATENT DOCUMENTS

| | | | |
|---|---|---|---|
| 5,798,031 A | 8/1998 | Charlton et al. | |
| 5,997,817 A | 12/1999 | Crismore et al. | |
| 6,004,441 A | 12/1999 | Fujiwara et al. | |
| 6,044,441 A | 3/2000 | Malinowski | |
| 6,238,597 B1 | 5/2001 | Yim et al. | |
| 6,309,526 B1 | 10/2001 | Fujiwara et al. | |
| 6,360,888 B1 | 3/2002 | McIvor et al. | |
| 7,527,716 B2 | 5/2009 | Harding | |
| 10,478,617 B2 * | 11/2019 | Pepin | H01B 3/307 |
| 2004/0178066 A1 | 9/2004 | Miyazaki et al. | |
| 2005/0258035 A1 | 11/2005 | Harding et al. | |
| 2005/0258050 A1 | 11/2005 | Harding | |
| 2008/0242962 A1 | 10/2008 | Roesicke et al. | |
| 2009/0020502 A1 | 1/2009 | Bhullar et al. | |
| 2011/0021889 A1 | 1/2011 | Hoss et al. | |
| 2012/0032910 A1 | 2/2012 | Kim et al. | |
| 2012/0078071 A1 * | 3/2012 | Bohm | A61B 5/14532 600/345 |
| 2012/0296444 A1 * | 11/2012 | Greenberg | A61N 1/0534 623/25 |
| 2013/0345780 A1 * | 12/2013 | Tabada | A61N 1/0529 607/115 |
| 2014/0005492 A1 | 1/2014 | Harrtig | |
| 2014/0163664 A1 * | 6/2014 | Goldsmith | A61B 17/12181 623/1.11 |
| 2015/0099954 A1 | 4/2015 | Achmann et al. | |
| 2015/0157862 A1 * | 6/2015 | Greenberg | H05K 3/4061 607/60 |
| 2019/0388013 A1 * | 12/2019 | Achmann | A61B 5/14532 |

FOREIGN PATENT DOCUMENTS

| | | |
|---|---|---|
| EP | 0 995 784 B1 | 9/2004 |
| EP | 1 972 269 A1 | 9/2008 |
| EP | 2 679 156 A1 | 1/2014 |
| EP | 3 086 629 A1 | 10/2016 |
| WO | WO 00/73785 A2 | 12/2000 |
| WO | WO 01/36953 A1 | 5/2001 |
| WO | WO 01/75438 A2 | 10/2001 |
| WO | WO 2009/056299 A1 | 5/2009 |
| WO | WO 2014/001382 A1 | 1/2014 |
| WO | WO 2016/160514 A1 | 10/2016 |

* cited by examiner

MEDICAL DEVICE AND METHOD FOR MANUFACTURING A MEDICAL DEVICE

RELATED APPLICATIONS

This application is a continuation of PCT/EP2018/057007, filed Mar. 20, 2018, which claims priority to EP 17 161 991.9, filed Mar. 21, 2017, the entire disclosures of each of which are hereby incorporated herein by reference.

BACKGROUND

This disclosure relates to a medical device and to a method for manufacturing a medical device. The devices and method according to this disclosure may mainly be used for long-term monitoring of an analyte concentration in a body fluid, such as for long-term monitoring of a blood glucose level or of the concentration of one or more other types of analytes in a body fluid. Further, the medical device and the method according to this disclosure may be used in any field of monitoring one or more body functions, such as for monitoring a physiological state of a body of a user, and, more preferably, for monitoring an analyte concentration in a body fluid of the user and/or for monitoring one or more other types of body functions, such as a heart rate, a blood pressure or other types of body functions. Preferably, the device according to this disclosure may be used for in vivo measurements of an analyte concentration in a body fluid of a user. However, other fields of application are possible.

In the field of medical technology, specifically in the field of monitoring health conditions of patients in hospitals or in the field of a home monitoring, a large number of devices for measuring one or more parameters related to one or more body functions is known. Thus, specifically, sensor elements for measuring heart rates, blood pressure or concentrations of one or more analytes in a body fluid of the user are known. In the following, without restricting the scope of this disclosure and without restricting the possibility of using other types of sensor units, this disclosure is mainly disclosed in the context of electrochemical sensor units capable of electrochemically measuring the concentration of one or more analytes in a body fluid, such as for measuring glucose in blood and/or interstitial fluid.

Thus, electrochemical tests are known, which are also referred to as electrochemical biosensors. Biosensors of this type mainly are used for qualitatively and/or quantitatively analyzing the content of biological liquids such as blood, plasma, interstitial fluid (ISF) or urine. The analyte which most widely is detected in the art is glucose. However, additionally or alternatively, detectors for other types of analytes are known, such as detectors for detecting lactate, PTT (partial thromboplastin), a pH value, urea, lipide, ethanol, cholesterol or other types of analytes. Examples for specific embodiments of electrochemical glucose sensor units are disclosed in U.S. Pat. Nos. 5,413,690, 5,762,770, 5,798,031, 5,997,817, U.S. Publication No. 2009/0020502 and WO 2009/056299.

In the art, for analyzing body fluids, so-called spot measurements are known, which require a sampling of a specific sample of a body fluid, which, subsequently, is analyzed by using a measurement device or sensor unit. Further, besides spot measurements, continuous measurements are known. Thus, specifically in the field of glucose measurement in the interstitial body tissue (interstitium), continuous measurement methods and devices are known, which are also referred to as CM devices. These continuous monitoring methods and devices are specifically useful for managing, monitoring and controlling specific types of illnesses such as a diabetes status. Meanwhile, implanted electrochemical sensor elements are used, which are also referred to or which may be embodied as so-called needle-type sensors or NTS. Therein, an active sensor portion having one or more electrodes is directly placed in the region of measurement, such as in the interstitial tissue. Further, by using one or more sensor electrodes or working electrodes having at least one detector substance having one or more enzymes, electrochemical in-situ or in-vivo measurements may be performed. Thus, as an example, enzymes such as glucose oxidase may be used, which are adapted for generating an electric charge, an electric current or an electric potential in the presence of glucose, from which the concentration of glucose may be derived and which may be used as a measurement signal or measurement information. Examples of these types of transcutaneous measurement systems are disclosed in U.S. Pat. No. 6,360,888 or in U.S. Publication No. 2008/0242962 A1.

Generally, continuous monitoring systems as known in the art are transcutaneous systems. As used herein, the term transcutaneous system refers to a device for monitoring the body function, wherein the device comprises a transcutaneous sensor unit. This transcutaneous sensor unit, preferably containing one or more electrodes, is placed beneath the skin of the user in a body tissue of the user. A part of the sensor unit may reach through the skin of the user, in order to be electrically connected to an electronic unit, which is also often referred to as an evaluation unit or patch and which generally may be adapted for controlling the sensor unit and/or for evaluating signals provided by the sensor unit. The evaluation unit generally may be located outside the body of the user, which may be a human or an animal. The device according to this disclosure also may optionally be embodied as a transcutaneous system. In transcutaneous systems, generally, the sensor unit is fully or partially inserted into the body tissue by using one or more inserters or insertion aids. Examples of inserters are disclosed in U.S. Pat. No. 6,360,888 B1. Other types of inserters are known. Typically, transcutaneous systems are worn by the user for a time period from several hours to several months or typically several days to several weeks, or, more typically, one week.

Specifically in the field of transcutaneous sensor systems, a large number of technical challenges referring to patterning of the substrates, assembly techniques, electrical contacting and packaging arise. Thus, needle-type sensors which are often used as sensor units for transcutaneous systems, generally require flexible, elongated substrates comprising fine conductive paths having a low electrical resistance. The flexibility of the sensor substrates as well as the requirement of high-definition patterning and reliable contacting of the sensor electrodes imposes a major technical challenge. Further, specifically in view of rising costs in the field of medical technology, cost-efficient manufacturing and assembly techniques are generally required.

In the field of sensor devices, several means and methods for contacting test elements are known. As an example, contacting of test strips via connector pins or spring contacts is disclosed in U.S. Pat. No. 7,527,716 B2. In EP 2 679 156 A1 a method for manufacturing a device for monitoring at least one body function of a user is disclosed.

In the art of electronics, specifically in the field of semiconductor manufacturing or in the field of manufacturing of integrated circuits (ICs), various printing techniques or patterning techniques are generally known, such as lithographic techniques or etching techniques. Further, a patterning of conductive paths and electrodes by laser ablation techniques is disclosed, e.g., in U.S. Pat. No. 6,044,441, in U.S. Pat. No. 6,309,526 B1, in WO 00/73785 A2, in WO 01/36953 A1, in WO 01/754438 A2 and in EP 1 152 239 A1. Further, printing techniques for electrode patterning are known, such as from U.S. Pat. No. 6,004,441. These techniques are generally limited by resolution. Further, anisotropic conductive adhesives are used for assembly of flip-chip-devices in integrated circuits, such as disclosed in EP 0 995 784 B1 or in U.S. Pat. No. 6,238,597 B1. Further, the use of anisotropic adhesives for contacting conductive polymeric electrodes in touch panel displays is disclosed in U.S. Publication No. 2012/0032910 A1.

Electrical contacts of a printed circuit board are usually realized by vias, specifically micro-vias. A double-sided contacting may lead to advantages during designing a surrounding hardware, such as a design of a connector which is configured to establish an electrical connection with both sides of the printed circuit board, respectively. Typically, a hole, such as a hole of 50 µm to 100 µm, may be prepared within the printed circuit board, such that the hole may be limited by a layer of the printed circuit board comprising copper. Thereafter, the holes may be copper-plated galvanically.

Despite the advantages implied by the techniques listed above, a large number of technical challenges remain in medical technology. Commonly, a usage of micro-vias may lead to disadvantages. Specifically, a large number of manufacturing steps may be necessary for manufacturing micro-vias. This may lead to increased production costs and to an increased production time. Further, a usage of biocompatible materials may be desired, specifically in invasive construction elements such as a glucose sensor having a flexible printed circuit board. However, commonly, micro-vias are made of copper.

SUMMARY

This disclosure provides a medical device and a method for manufacturing a medical device which at least partially avoids the shortcomings of known devices and methods of the kind just discussed and which at least partially address the above-mentioned challenges. Specifically, devices are disclosed herein which allow for easy and efficient and, still, reliable manufacturing of medical devices such as sensor devices for continuous monitoring of one or more analytes in a body fluid.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. Further, it shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "conductive layer," "electrical contact" and "electrical connector," to name only a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

As generally used within this disclosure, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, this disclosure may be applied to other types of users or patients or diseases.

The term "body tissue" may generally refer to a cellular organizational level intermediate between cells and a complete organ. The body tissue may specifically be an ensemble of similar cells from the same organ that together carry out a specific function. Thereby, organs may then be formed by functional grouping together of multiple tissues. As an example for body tissue, interstitial tissue, i.e., connective tissue between cellular elements of a structure, may be named or the interstitial tissue which can be part of, close to or underneath the skin. As further used herein, the term "body fluid" generally may refer to a fluid which is typically present in a body or the body tissue of the user or the patient and/or which may be produced by the body of the user or the patient. Thus, as an example, the body fluid may be selected from the group consisting of blood and interstitial fluid. However, additionally or alternatively, one or more other types of body fluids may be used, such as saliva, tear fluid, urine or other body fluids.

In a first aspect of this disclosure, a medical device is disclosed. The medical device comprises at least one first part. The first part comprises at least one interconnect device. The interconnect device comprises at least one first conductive layer; at least one insulation layer and at least one second conductive layer. The second conductive layer is separated from the first conductive layer at least by the insulation layer. The at least one insulation layer, as an example, may form an insulating substrate.

The medical device further comprises at least one electrical contact. The electrical contact may be embodied as a part of the first part or as an independent electrical contact. The electrical contact comprises at least one electrical contact material and as will be outlined in further detail below, the electrical contact material may be made of or may comprise a conductive paste. The electrical contact is electrically connected to the second conductive layer. The electrical contact is contactable from one side of the interconnect device opposing the second conductive layer, e.g., relative to the insulation layer. Thus, the one side of the interconnect device and the second conductive layer oppose each other. In particular, the one side of the interconnect device, which opposes the second conductive layer, may oppose the second conductive layer, such as relative to the insulation layer. Herein, the expression "relative to the insulation layer" may be understood as emphasizing the fact that the two opposing objects of the one side of the interconnect device and the second conductive layer are separated by the insulation layer. Thus, the electrical contact may be contactable from one side of the interconnect device opposing the second conductive layer relative to the insulation layer. In other words, the electrical contact may be contactable from one side of the interconnect device wherein the side of the interconnect device is opposed to the second conductive layer relative to the insulation layer. The electric contact is provided micro-via free.

Further, the medical device comprises at least one second part. The second part comprises at least one electrical connector. Further, the second part is configured to mate with the first part and to establish an electrical connection between the electrical connector of the second part and the first conductive layer and to further establish an electrical connection between the electrical connector of the second part and the second conductive layer via the electrical contact.

Thus, as will be outlined in further detail below, the electrical contact allows for electrically contacting both the first conductive layer and the second conductive layer from the same side of the insulation layer of the first part, even though the first conductive layer and the second conductive layer are located on opposing sides of the insulation layer. As an example, the first conductive layer may comprise at least one first contact pad located on a first side of the insulation layer, and the second conductive layer may comprise at least one second contact pad located on a second side of the insulation layer, opposing the first side. The electrical contact, such as the electrical contact paste, allows for contacting both the first contact pad and the second contact pad from the same side, e.g., from the first side. Therein, preferably, the electrical contact does not contain any vias reaching through the insulation layer. Instead, as will be outlined in further detail below, basically, two concepts may be used alternatively or even in combination:

a) A first concept in which the electrical contact, such as a conductive paste, extends over an edge of the insulation layer, such that a portion of the electrical contact is located on the first side of the insulation layer, i.e., on the same side as the first conductive layer, and a further portion of the electrical contact is located on the second side, contacting the second conductive layer. Thus, on the first side, both the first conductive layer and a portion of the electrical contact between connected to the second conductive layer may be contacted electrically.

b) A second concept in which the electrical contact, such as the conductive paste, forms a layer, specifically a flat layer, on which the first part may rest, with the second conductive layer being electrically contacting the layer, and with the layer extending laterally over the insulation layer. In this case, as an example, the at least one electrical connector of the second part may comprise a first electrical connector, electrically contacting the first layer, and a second electrical connector electrically contacting at least a part of the layer of the electrical contact extending laterally over the insulation layer.

In accordance with the second concept, the medical device may specifically comprise the following setup, in the given order:

the layer of the electrical contact,
the second conductive layer being in electrical contact with the layer of the electrical contact,
the insulation layer,
the first conductive layer.

When referring to a number of elements or objects that are given in the form of a list, the expression "in the given order" may, generally describe a sequential arrangement of these elements in a setup or in an array, wherein the sequential arrangement of the elements is in agreement with the order in which the elements appear in the list. Thus, the relation, which any two elements may have to each other within the list is reflected in the sequential arrangement of these elements in the setup or array. Thus, two elements that on the list are separated by a third element, may be separated at least by that same third element in the setup or array. Specifically, in other words, the layer of the electrical contact may be followed by the second conductive layer being in electrical contact with the layer of the electrical contact, and the second conductive layer may be followed by the insulation layer, which again may be followed by the first conductive layer.

As further used herein, the term "medical device" may generally refer to an arbitrary device configured for conducting at least one medical analysis and/or at least one medical procedure. The medical device therefore may generally be an arbitrary device configured for performing at least one diagnostic purpose and/or at least one therapeutic purpose. In the following, without restricting further embodiments, this disclosure mainly will be described in terms of a medical device configured for performing at least one diagnostic purpose and, specifically, a medical device comprising at least one analyte sensor for performing at least one analysis. The medical device generally may also be or may comprise at least one of a sensor assembly, a sensor system, a sensor kit or a sensor device, preferably the medical device is a continuous glucose monitoring sensor assembly, sensor system, sensor kit or sensor device such as Abbott Freestyle Libre®, Dexcom G5® CGM System or Roche Accu-Chek Insight CGM. The medical device may specifically be a compact, wearable or portable device which may be carried by a user, such as a device having a volume of less than 1000 $cm^3$ or even less than 500 $cm^3$, and/or having a weight of less than 500 g, preferably of less than 200 g. Specifically, the device may fully or partially be carried on a body surface of the body of the user. The medical device may be configured for monitoring at least one body function of the user. However, other applications may be feasible.

The terms "first part" and "second part" may be considered as nomenclature only, without numbering or ranking the named elements, without specifying an order and without excluding a possibility that several kinds of first parts and second parts may be present. Further, additional parts such as one or more third parts may be present. The term "part" may refer to an arbitrary component of an object. The component may be configured for interacting with a further component of the object. Specifically, the first part and the second part of the medical device may be capable of interacting with each other, such as in order to perform one or more diagnostic and/or therapeutic purposes, such as in order to perform the medical analysis and/or the medical procedure as outlined above. Specifically, the first part and the second part may be capable of performing at least one detection of the at least one analyte in the body fluid and/or in order to contribute to the at least one detection of the at least one analyte in the body fluid. However, other embodiments may be feasible.

Exemplarily, the first part of the medical device may be a sensor unit and the second part may be a sensor electronic unit, specifically an evaluation unit. As further used herein, the term "sensor unit" may refer to an arbitrary element which is adapted to perform a process of detection and/or which is adapted to be used in the process of detection. Thus, the sensor unit may specifically be adapted to determine the concentration of the analyte and/or a presence of the analyte. The sensor unit may also be referred to as "sensor" or "analyte sensor." As will be outlined in further detail below, the sensor unit specifically may be fully or partially implantable into a body tissue of a user or patient. The term "detection" may generally refer to a process of determining a presence and/or a quantity and/or a concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal.

The sensor unit specifically may be an electrochemical sensor. As used herein, an "electrochemical sensor" generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates the presence and/or the extent of the electrochemical detection reaction, such as at least one current and/or at least one voltage. The sensor unit sensor may comprise at least two electrodes, such as at least one working electrode and at least one counter electrode. As used herein, the term "working electrode" may refer to an electrode being adapted for or being usable for performing at least one electrochemical detection reaction for detecting the at least one analyte in the body fluid. The working electrode may have at least one test chemical being sensitive to the analyte to be detected. The term "test chemical" specifically may refer to an arbitrary material or a composition of materials adapted to change at least one detectable property in the presence of at least one analyte. This property may be an electrochemically detectable property. Specifically, the at least one test chemical may be a highly selective test chemical, which only changes the property if the analyte is present in the body fluid whereas no change occurs if the analyte is not present. The degree or change of the at least one property is dependent on the concentration of the analyte in the body fluid, in order to allow a quantitative detection of the analyte. As an example, the test chemical may comprise at least one enzyme, such as glucose oxidase and/or glucose dehydrogenase. As used herein, the term "counter electrode" may refer to an electrode adapted for performing at least one electrochemical counter reaction and adapted for balancing a current flow required by the detection reaction at the working electrode.

However, additionally or alternatively, other types of sensor units may be comprised, such one or more of a sensor unit for detecting a heart rate, such as by detecting appropriate movements due to a heartbeat, a blood pressure measurement unit, a temperature sensor, a pH sensor or any other types of sensor units or combinations thereof.

The sensor unit may comprise at least one implantable sensor unit. Specifically, the implantable sensor unit may comprise at least one implantable portion configured for full or partial implantation into a body tissue of a user, such as by transcutaneous insertion. The term "implantable portion" may generally refer to a property of an arbitrary portion of an element of being adapted to be fully or at least partly arranged through the body tissue of the patient or the user. Thus, the sensor unit may also be referred to as transcutaneous sensor unit. The implantable portion may fully or partially provide a biocompatible surface, i.e., a surface which, at least during durations of use, does not have any detrimental effects on the user, the patient or the body tissue, e.g., by having a biocompatible coating. Further, the implantable portion generally may be dimensioned such that a transcutaneous insertion of the element into the body tissue is feasible, such as by providing a width in a direction perpendicular to an insertion direction of no more than 5 mm, preferably of no more than 2 mm, more preferably of no more than 1.5 mm. Thus, the term "subcutaneous" may generally refer to a property of an arbitrary element of being situated or lying under the skin and within the body tissue of the user or the patient. Specifically, the object may be configured to be introduced under the skin, exemplarily as an injection.

The term "sensor electronic unit" may generally refer to an arbitrary one-component or multi-component element or device adapted for processing data such as for acquiring measurement values and, optionally, for fully or partially evaluating the measurement values. Therefore, the sensor electronic unit may also be referred to as evaluation unit. Specifically, the sensor electronic unit may be configured for interacting with the sensor unit and/or for controlling the sensor unit. As an example, reference may be made to the sensor electronic unit as disclosed in EP1972269A1 and the sensor unit disclosed therein. Still, other embodiments are feasible.

As further used herein, the term "interconnect device" may refer to an arbitrary device which is configured to mechanically support and/or to electrically connect electronic components such as by using tracks and/or pads. The interconnect device may specifically comprise at least one electrically insulating material. The electrically insulating material may form a substrate for the electronic components. As an example, the interconnect device may have a flat shape. The interconnect device may have a lateral extension exceeding its thickness by at least a factor of 2, at least a factor of 5, at least a factor of 10, or even at least a factor of 20 or more. The interconnect device specifically may have an elongated shape, such as a strip-shape and/or a bar-shape. The interconnect device may also be referred to as circuit board and/or as printed circuit board.

Specifically, the interconnect device may be a copper-free interconnect device. The term "copper-free" may refer to a property of an arbitrary object of being completely or at least to a large extent, like at least 90%, at least 95% or at least 99%, free from copper and/or chemical compounds comprising copper. The interconnect device may comprise one or more components and all of the components or at least most of the components may be completely or at least to a large extent free from copper and/or chemical compounds comprising copper. Specifically, at least one of the insulation layer, the first conductive layer, the second conductive layer, the electrical contact may be completely or at least to a large extent free from copper and/or chemical compounds comprising copper.

Further, the interconnect device may be a flexible interconnect device. The term "flexible" may generally refer to a property of an arbitrary object of being bendable, usually without breaking, and preferably reversibly bendable. Specifically, the flexible interconnect device may be bendable with a bending radius of 1 mm. The flexible interconnect device may further have or may further support a pre-bending of 60°. Furthermore, the flexible interconnect device may have or may support a deflection of at least 10°. Specifically, a bending procedure, such as but not limited to the application of a bending radius, a pre-bending and/or a deflecting, may be applied to the flexible interconnect device and reversed in at least 10000 cycles before the flexible interconnect device breaks. Thus, after at least 10000 cycles the flexible interconnect device may lose its flexibility and/or may fracture. The interconnect device may comprise at least one flexible substrate and electrical components of the interconnect device may be deposited on the flexible substrate. As an example, the substrate may comprise a flexible or deformable plastics material, such as a polyimide material, e.g., a polyimide foil. Thereby, the electrical components of the interconnect device may be made of flexible materials and/or of rigid materials. Specifically, the insulation layer of the interconnect device may be a flexible insulation layer. However, other embodiments may also be feasible.

As further used herein, the term "layer" may refer to an arbitrary covering of an arbitrary substrate, specifically of a flat substrate. The layer may specifically have a lateral extension exceeding its thickness by at least a factor of 2, at least a factor of 5, at least a factor of 10, or even at least a factor of 20 or more. The layer may be patterned or unpatterned. As an example, the first and second conductive layers each, independently, may be unpatterned or each may be patterned such that the first conductive layer and/or the second conductive layer comprises at least one contact pad.

As further used herein, the term "insulation layer" may refer to an arbitrary layer which comprises or is at least partially, e.g., fully or partially, made of at least one insulating material. The term "insulating material" may refer to an arbitrary material whose internal electric charges do not flow freely, and therefore make it nearly impossible to conduct an electric current under the influence of an electric field. Thus, the insulating material may have higher resistivity than semiconducting materials or conducting materials. Specifically, the insulation layer may comprise at least one material selected from the group consisting of: a solder mask; a flexible solder mask; a varnish; an acrylic varnish, in particular NPR-80 and/or ID100; a two-component acrylic varnish; a hardener, in particular PF10/ID36. In a preferred embodiment, the insulation layer may comprise a flexible solder mask comprising a two-component acrylic varnish, wherein a first component comprises NPR-80 and a second component comprises ID100, and a hardener, wherein the hardener comprises PF10/ID36. Further, the insulation layer may have a thickness of 15 µm to 30 µm.

The insulation layer may form a substrate for at least one of the first conductive layer, the second conductive layer. The term "substrate" may refer to an arbitrary element which is suitable to carry one or more other elements disposed thereon or therein. As an example, the substrate may be a flat substrate, such as a substrate having a lateral extension exceeding its thickness by at least a factor of 2, at least a factor of 5, at least a factor of 10, or even at least a factor of 20 or more. The substrate specifically may have an elongated shape, such as a strip-shape and/or a bar-shape. However, other embodiments may be feasible. Further, the insulation layer may be an insulating carrier material layer. The term "carrier material layer" may refer to an arbitrary layer which is configured to mechanically support one or more components and/or one or more coatings disposed thereon. Specifically, the insulating carrier material layer may be configured to mechanically support the first conductive layer, the second conductive layer and/or the electrical contact. Further, the insulating carrier material layer may be configured to mechanically support further components of the interconnect device such as further layers of the interconnect device.

The terms "first conductive layer" and "second conductive layer" may be considered as nomenclature only, without numbering or ranking the named elements, without specifying an order and without excluding a possibility that several kinds of first conductive layers and second conductive layers may be present. Further, additional conductive layers such as one or more third conductive layers may be present. The term "conductive layer" may refer to an arbitrary layer which comprises or is at least partially, e.g., fully or partially, made of at least one conductive material. The term "conductive material" may refer to an arbitrary material that allows a flow of an electrical current in one or more directions. Thereby, the electrical current may be generated by a flow of negatively charged electrons, positively charged holes, positive ions and/or negative ions. However, other embodiments may be feasible. The first conductive layer and/or the second conductive layer may comprise at least one material selected from the group consisting of: gold and carbon. The first conductive layer and the second conductive layer may comprise or may be of the same material. The first conductive layer and/or the second conductive layer may have an electrical resistance of 0.5 Ohm to 10 Ohm. In particular, the first conductive layer and the second conductive layer may have the same electrical conductivity. The first conductive layer and the second conductive layer may be inert towards potentials and/or currents applied.

The first conductive layer and/or the second conductive layer may have a thickness of 50 nm to 4 µm, preferably of 100 nm to 3 µm, more preferably of 200 nm to 2 µm. Specifically, the thickness of the first conductive layer and the thickness of the second conductive layer may be identical.

The first conductive layer and/or the second conductive layer may be applied onto the insulation layer such that at least one coating is formed on at least one surface of the insulation layer. The insulation layer may comprise polyimide. As further used herein, the term "coating" may refer to an arbitrary covering which is applied to at least one surface of an arbitrary object. The coating may cover the object completely or may only cover a part or parts of the object. The coating may be applied by a coating process, such as a wet-chemical coating, a printing process, a blade coating, a spraying process, a dispensing process, a tampon-printing process, a galvanization process, a sputtering process, a vapor deposition process, a screen printing process, a stencil printing process or the like.

The first conductive layer and/or the second conductive layer may be formed on at least one surface of the insulation layer. The first conductive layer and/or the second conductive layer may cover the surface completely or may only cover a part or parts of the surface. Further, the first conductive layer and/or the second conductive layer may be formed as a continuous layer. Thereby, the continuous layer may be formed as one unit wherein the continuous layer is at least to a large extent free from interruptions.

The first conductive layer and/or the second conductive layer may comprise gold. The insulation layer may comprise polyimide. In a preferred embodiment, the first conductive layer and/or the second conductive layer may be a gold layer and the insulation layer may be a polyimide layer. The gold layer may be applied to the polyimide layer by a galvanization process. In this case, a copper layer may be located between the polyimide layer and the gold layer. The copper layer may serve as an adhesion promoter. Thus, the first conductive layer and/or the second conductive layer may be completely or in sections separated from the insulation layer by the copper layer. Alternatively, the gold layer may be applied to the polyimide layer by a sputtering process and/or a vapor deposition process. In this case, a palladium layer may be located between the polyimide layer and the gold layer. The palladium layer may serve as an adhesion promoter. Thus, the first conductive layer and/or the second conductive layer may be completely or in sections separated from the insulation layer by the palladium layer.

The first conductive layer and/or the second conductive layer may comprise carbon. In another preferred embodiment, the first conductive layer and/or the second conductive layer may be a carbon layer and/or a carbon-comprising layer and the insulation layer may be the polyimide layer. The carbon layer and/or the carbon-comprising layer may be applied directly onto the polyimide layer, e.g., by a screen printing process and/or a stencil printing process. In particular, the carbon layer may be applied as a carbon paste and the carbon-comprising layer may be applied as a carbon-comprising paste.

As outlined above, the second conductive layer is separated from the first conductive layer at least by the insulation layer. The term "being separated from" may refer to a property of two or more arbitrary elements of being set apart, disconnected or dissociated from each other. Thus, the two or more elements may be arranged in a distance to each other. Specifically, the two or more elements may not be in direct contact with each other. The first conductive layer and the second conductive layer may be disposed on the insulation layer. Specifically, the first conductive layer and the second conductive layer may be disposed on the at least one surface of the insulation layer. The insulation layer may comprise at least one first insulation layer surface and at least one second insulation layer surface, wherein the first insulation layer surface and the second insulation layer surface may extend along a direction of extension of the interconnect device and/or along the direction of extension of the insulation layer. The direction of extension may specifically refer to a direction along a longitudinal direction along a longitudinal axis and/or to a direction along a transverse axis of the interconnect device. The first insulation layer surface may be located on a first insulation layer side of the insulation layer and the second insulation layer surface may be located on a second insulation layer side of the insulation layer. Thus, the insulation layer may be located between the first conductive layer and the second conductive layer. Specifically, the insulation layer may be configured to act as a spacer between the first conductive layer and the second conductive layer. Thus, the first conductive layer and the second conductive layer may be arranged in a distance to each other.

The term "side" may refer to a part of an arbitrary object, specifically to a surface of the object, which forms an outside of the object. The side may exemplarily be separated from other sides of the object by one or more edges and/or corners. However, other embodiments may be feasible. Specifically, the objects may comprise a plurality of sides, e.g., two or more sides, such as one or more front sides, reverse sides, top sides, bottom sides and/or lateral sides. The terms "first insulation layer side" and "second insulation layer side" may be considered as nomenclature only, without numbering or ranking the named elements, without specifying an order and without excluding a possibility that several kinds of first insulation layer sides and second insulation layer sides may be present. Further, additional insulation layer sides such as one or more third insulation layer sides may be present. Further, the terms "first insulation layer surface" and "second insulation layer surface" may be considered as nomenclature only, without numbering or ranking the named elements, without specifying an order and without excluding a possibility that several kinds of first insulation layer surfaces and second insulation layer surfaces may be present. Further, additional insulation layer surfaces such as one or more third insulation layer surfaces may be present.

Moreover, the interconnect device may comprise at least one further layer. In particular, the at least one further layer may be an electrically conductive layer. In particular, the interconnect device may comprise at least 20, preferably at least 30 further layers.

As outlined above, the interconnect device comprises the at least one electrical contact. The term "electrical contact" may generally refer to an arbitrary element such as an electrical circuit component of an arbitrary electrical circuit which is configured to pass an electrical current. As outlined above and as outlined in further detail below, the electrical contact specifically may fully or partially be made of at least one electrically conductive paste. The electrical contact specifically may extend over an edge of the insulation layer, thereby electrically connecting a second side of the insulation layer, with the second conductive layer, with a first side of the insulation layer, allowing to contact both the first layer and the second layer from the first side, or, alternatively, the electrical contact may form a layer on the side of the second conductive layer, extending laterally over the insulation layer, thereby allowing for electrically contacting the first conductive layer from the first side and, further, also electrically contacting the second conductive layer from the first side, via the layer of the electrical contact.

In case the electrical contact is electrically connected with a further electrical contact, the electrical current may flow from the electrical contact to the further electrical contact or vice versa. In case the electrical contact is separated from the further electrical contact by an insulating gap such as air, vacuum or an insulating material, the electrical current is not passed. As outlined above, the electrical contact comprises at least one electrical contact material. The term "electrical contact material" may refer to an arbitrary material that allows a flow of an electrical current in one or more directions. Thereby, the electrical current may be generated by a flow of negatively charged electrons, positively charged holes, positive ions and/or negative ions. However, other embodiments may be feasible. Thus, the electrical contact material may also be referred to as "conductive material." Specifically, the electrical contact material may have an electric conductivity of at least 0.01 S/m, preferably of at least 0.1 S/cm, more preferably of at least 1.0 S/cm and most preferably of at least 100 S/cm. Exemplarily, the electrical contact material may comprise at least one material selected from the group consisting of: silver, silver chloride and carbon. Specifically, the electrical contact material may be copper-free. The electrical contact material may comprise one or more components and all of the components or at least most of the components may be completely or at least to a large extent free from copper and/or chemical compounds comprising copper.

Specifically, the electrical contact material may comprise an electrically conductive paste or may be applicable to the interconnect device as an electrically conductive paste, e.g., as one or more of a silver paste, a silver chloride paste or a carbon paste. Specifically, the electrical contact material may comprise or may be a dried electrically conductive paste. The term "paste" may refer to an arbitrary viscous fluid. The term "viscosity" may refer to a resistance of an arbitrary fluid to a gradual deformation by shear stress or tensile stress. Specifically, viscosity may be a property of the fluid which opposes a relative motion between at least two surfaces of the fluid which are moving at different velocities. Generally, a fluid which has no resistance to shear stress may be known as an ideal or an inviscid fluid. Zero viscosity may only be observed at very low temperatures in superfluids. Thus, the paste may refer to a heterogeneous mixture comprising at least one medium, specifically at least one fluidic medium, as well as particles, specifically solid particles. The particles may specifically be larger than one micrometer. Thus, the particles do not dissolve but get suspended throughout a bulk of the fluid medium. The term "electrically conductive paste" may refer to a paste which comprises at least one electrically conductive material. The electrically conductive material may specifically be provided as particles, specifically as electrically conductive particles, which are dispersed within a fluidic medium. Thus, the electrically conductive paste may comprise at least one of a suspension and a dispersion of the electrical contact material. Specifically, the electrical contact material may be provided as the conductive paste. The conductive paste may be applied on at least one part of at least one of the first conductive layer, the insulation layer and the second conductive layer, as will further be described below in more detail. Specifically, the first conductive layer, the insulation layer and the second conductive layer may form at least one substrate and the conductive paste is configured to be applied to at least one part of the substrate. The fluidic medium of the conductive paste may be configured to evaporate completely or at least to a large extent, specifically via one or more drying processes, and the electrically conductive particles may form a film on the part of the substrate, specifically a continuous film. Thereby, the continuous film may be formed as one unit wherein the continuous film is at least to a large extent free from interruptions. Specifically, the continuous film may be formed such that the electrically conductive particles are in electrical contact with each other such that a flow of an electrical current in one or more directions is allowed. Thereby, the electrical current may be generated by a flow of negatively charged electrons, positively charged holes, positive ions and/or negative ions. However, other embodiments may be feasible. Specifically, the electrically conductive particles may be in direct contact with each other, e.g., the electrically conductive particles may touch each other.

As outlined above, the electrical contact is electrically connected to the second conductive layer. As further used herein, the term "electrically connected" may refer to a property of two or more electrically conductive elements of being arranged relative to each other such that a flow of an electrical current in one or more directions between the two or more electrically conductive elements is allowed. Exemplarily, one element of the two or more electrically conductive elements may be in direct contact with at least one further element of the two or more electrically conductive elements. Specifically, the element and the further element may touch each other. However, other embodiments may be feasible. Exemplarily, the element and the further element may be arranged in a distance to each other, and another electrically conductive object such as a third element may be arranged between the element and the further element such that a flow of the electrical current is allowed between the element and the further element through or via the third element. Thus, the third element may also be referred to as linking element or connecting element. Specifically, the electrical contact material may be in direct contact with at least one surface of the second conductive layer.

Exemplarily, the interconnect device may have at least one edge. The term "edge" may refer to a line of an arbitrary object at which at least two surfaces of a solid object meet. Specifically, the edge may refer to a type of line segment joining two vertices in a polygon, polyhedron, or higher-dimensional polytope. In a polygon, the edge may refer to a line segment on a boundary. In a polyhedron or more generally a polytope, an edge may refer to a line segment where two surfaces meet. Specifically, the electrical contact material may extend over the edge of the interconnect device. As further used herein, the term "extending over an edge" may refer to a property of an arbitrary element of covering an edge of another object at least partially, e.g., fully or partially. Specifically, the element may cover at least two surfaces of the object which meet at the edge and the element may cover the edge as well. Specifically, the second conductive layer may be located on, e.g., disposed on and/or attached to, the second insulation layer side of the insulation layer, the second insulation layer side opposing the first insulation layer side. The electrical contact and the first conductive layer both may be at least partially located on, e.g., disposed on and/or attached to, the first insulation layer side.

The electrical contact material may be at least partially located on at least one insulation layer surface of the insulation layer. Specifically, the insulation layer surface may comprise the at least one first insulation layer surface and the at least one second insulation layer surface as outlined above. The first insulation layer surface and the second insulation layer surface may extend along the direction of extension of the interconnect device. Specifically, the first insulation layer surface and the second insulation layer surface may be parallel to each other. The first conductive layer may cover the first insulation layer surface at least partially. Further, the second conductive layer may cover the second insulation layer surface at least partially. The term "covering" may refer to a condition of an arbitrary material if being located on, disposed on and/or attached to a surface of an arbitrary object.

Further, the insulation layer may comprise at least one third insulation layer surface. The third insulation layer surface may extend along a direction transverse, specifically perpendicular, to the direction of extension of the interconnect device. Specifically, the third insulation layer surface may refer to a narrow side of the insulation layer. The term "third insulation layer surface" may be considered as nomenclature only, without numbering or ranking the named element, without specifying an order and without excluding a possibility that several kinds of third insulation layer surfaces may be present. Further, additional insulation layer surfaces such as one or more fourth insulation layer surfaces may be present. The electrical contact material may cover the third insulation layer surface at least partially, e.g., fully or partially. Specifically, the electrical contact material may form a continuous film on the third insulation layer surface.

The second conductive layer may cover the second insulation layer surface at least partially. Specifically, the second conductive layer may be fitted flush to the insulation layer. Thereby, the second conductive layer may end with the second insulation layer surface. Specifically, the second conductive layer may have a perpendicular second conductive layer surface which extends transverse, specifically perpendicular, to the direction of extension of the interconnect device. The perpendicular second conductive layer surface may be fitted flush to the third insulation layer surface. The perpendicular second conductive layer surface and the third insulation layer surface may be arranged along a line, specifically along a straight line. The perpendicular second conductive layer surface and the third insulation layer surface may form a narrow side of the interconnect device or may be part of the narrow side of the interconnect device. Specifically, the electrical contact material may cover the perpendicular second conductive layer surface at least partially.

Moreover, the electrical contact material may cover the first insulation layer surface at least partially, preferably partially. The first conductive layer and the electrical contact material may both cover the first insulation layer surface. Specifically, the first conductive layer may cover a first section of the first insulation layer surface and the electrical contact material may cover a second section of the first insulation layer surface. The first section and the second section may specifically be distinct from each other, e.g., the first section and the second section may refer to different sections or parts of the first insulation layer surface. The first section and the second section be are arranged in a distance to each other. Specifically, the first section and the second section may not overlap with each other or touch each other. However, other embodiments may be feasible. Specifically, the first conductive layer and the electrical contact material may be oriented relative to each other, such that a gap is formed on the first insulation layer surface. The term "gap" may refer to an empty space of an arbitrary object or between two or more arbitrary objects. Specifically, the gap may have or may be embodied as a recess or as a cavity of the object or between the two or more objects. Exemplarily, the gap may be formed at least by the first insulation layer surface, at least one first conductive layer surface which is oriented transverse, specifically perpendicular, to the direction of extension of the interconnect device, and at least one electrical contact material surface of the electrical contact material which is oriented transverse, specifically perpendicular, to the direction of extension of the interconnect device. The electrical contact material surface and the first conductive layer surface may be parallel to each other. However, other embodiments may be feasible. The gap has a rectangular shape, specifically a square shape.

As outlined above, the electrical contact is contactable from one side of the interconnect device opposing the second conductive layer, such as relative to the insulation layer. The interconnect device may comprise at least one first interconnect device side and at least one second interconnect device side. The terms "first interconnect device side" and "second interconnect device side" may be considered as nomenclature only, without numbering or ranking the named elements, without specifying an order and without excluding a possibility that several kinds of first interconnect device sides and second interconnect device sides may be present. Further, additional interconnect device sides such as one or more third interconnect device sides may be present. The first interconnect device side may refer to a side of the interconnect device which is at least partially covered by first conductive layer and the second interconnect device side may refer to a side of the interconnect device which is at least partially covered by the second conductive material. Thus, the electrical contact may be contactable from the first interconnect device side. However, also other embodiments may be feasible.

As outlined above, the electrical contact is provided micro-via free. The term "via", also referred to as vertical interconnect access, may refer to an arbitrary electrical connection between layers in an electronic circuit such as an interconnect device or a printed circuit board which goes through a plane of one or more adjacent layers. Specifically, a via may comprise at least two pads in corresponding positions, e.g., in opposite positions, on different layers of the interconnect device which may be electrically connected by a hole through the interconnect device. The hole may be made conductive by electroplating, or may be lined with a tube or a rivet. Further, the term "micro-via" may refer to a via in high-density multi-layer printed circuit boards and may be configured to accommodate a high input density and/or output density of advanced packages. The micro-via may be embodied as a blind via and/or a buried via. The blind via may be exposed only on one side of the printed circuit board. Further, the buried via may be configured to connect internal layers without being exposed on either surface of the printed circuit board. The term "micro-via free" may generally refer to a property of an arbitrary interconnect device such as a printed circuit board of being completely or at least to a large extent free from vias, specifically micro-vias, more specifically buried vias and/or blind vias. Thus, specifically, the interconnect device may not comprise any vias, specifically micro-vias, more specifically buried vias and/or blind vias.

As outlined above, the second part comprises the at least one electrical connector. The term "electrical connector" may refer to an arbitrary electrical device configured for electrically contacting another electrical device. As an example, the electrical connector may be or may comprise one or more of an electrical contact pad, an electrical spring contact, an electrical contact pin. Other types of electrical contact are feasible. The electrical connector may be electrically contactable via soldering, wirebonding, flip chip mounting, or probe needles. However, other embodiments may be feasible. The electrical connector specifically may be comprised of a conductive material such as at least one metal. The electrical connector may form an end portion of a conductive path or may be connected to an end portion of a conductive path, specifically a conductive path applied to a substrate of the second part. The electrical connector may have or may be a round or rectangular or rounded pad, specifically applied to the substrate of the second part. However, other embodiments may be feasible. Additionally or alternatively, the electrical connector may comprise a spring contact or a contact pin which may be pressed onto another electrical element, such as onto the electrical contact, e.g., a surface area of electrically conductive paste, in order to generate an electrical connection between the electrical connector and the electrical element.

The term "mating" may refer to a process of connecting and/or linking two or more elements with each other. The two or more elements may be brought in close proximity to each other and may be attached, specifically fixedly attached, to each other such as via a form-fit and/or force-fit connection. Exemplarily, the first part and the second part may be attached to each other via at least one adhesive material. However, other embodiments may be feasible. The electrical connector of the second part and the electrical contact may overlap in an overlap area of 1 $mm^2$ to 50 $mm^2$, preferably of 5 $mm^2$ to 20 $mm^2$ and most preferably in an overlap area of 15 $mm^2$. Additionally or alternatively, the electrical connector may be or may comprise a spring contact or a contact pin which may be pressed onto the electrical contact, e.g., onto a surface area of the electrical contact.

As outlined above, the second part is configured to mate with the first part and to establish an electrical connection between the electrical contact pad of the second part and the first conductive layer and to establish an electrical connection between the electrical connector and the second conductive layer via the electrical contact. Thus, as discussed above, the electrical connector may comprise at least one first electrical connector forming at least one first electrical connection with the first conductive layer and may further comprise at least one second electrical connector forming at least one second electrical connection with the second conductive layer. The first and second electrical connections may be made from the same side of the insulation layer, such as from the side of the insulation layer having the first conductive layer.

The term "electrical connection" may refer to a connection between two or more electrically conductive elements such that a flow of an electrical current between the two or more elements is allowed in one or more directions. Thus, the two or more elements may be in electrical contact with each other.

In a further aspect of this disclosure, a method for manufacturing a medical device is disclosed. The method comprises the method steps as given in the independent claims and as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method comprises the following steps:
a) providing at least one first part of the medical device, by providing at least one insulation layer having at least one first conductive layer and at least one second conductive layer disposed thereon, wherein the second conductive layer is separated from the first conductive layer at least by the insulation layer;
b) providing at least one electrical contact, wherein the electrical contact comprises at least one electrical contact material, specifically at least one electrically conductive paste or at least one light electrically conductive paste, wherein the electrical contact is arranged such that it is contactable from a side of the first part opposing the second conductive layer, wherein the electrical contact is provided micro-via free;
c) electrically connecting the electrical contact to the second conductive layer;
d) providing at least one second part of the medical device, the second part having at least one electrical connector; and
e) mating the second part with the first part and establishing an electrical connection between the electrical connector of the second part and the first conductive layer and establishing an electrical connection between the electrical connector and the second conductive layer via and the electrical contact.

In step b), the electrical contact, such as the conductive paste, may be placed directly on the insulation layer, specifically on one part of the insulation layer. Additionally or alternatively, however, the electrical contact, e.g., a layer of the conductive paste, may also be placed on at least one support surface of the medical device separate from the insulation layer, thereby, e.g., forming the above-mentioned layer.

Specifically, the conductive paste may be placed on the part of the insulation layer such that the conductive paste is in direct contact with the second conductive layer. Further, the conductive paste may be placed on the part of the insulation layer such that the conductive paste covers the insulation layer at least partially. Moreover, the conductive paste may be placed on the part of the insulation layer such that the conductive paste and the first conductive layer are oriented relative to each other and such that a gap between the first conductive layer and the conductive paste emerges. Further, the conductive paste may be placed on the part of the insulation layer such that the conductive paste covers at least one edge of the insulation layer at least partially. The conductive paste may be placed on the part of the insulation layer such that the conductive paste covers the insulation layer at least partially and such that the conductive paste covers the second conductive layer at least partially, preferably at least one second conductive layer surface of the second conductive layer which extends perpendicular to a direction of extension of the insulation layer.

The conductive paste may comprise at least one material selected from the group consisting of silver, silver chloride and carbon and the material may be dispersed in at least one solvent, preferably at least one organic solvent. The solvent may be selected from the group consisting of: diethylene glycol monobutyl ether; propanol; ethanol and tetrahydrofuran. The conductive paste may specifically be centrifuged, preferably vacuum centrifuged, before the conductive material is applied to the interconnect device. Other mixing procedures including mixing procedures using at least one stirrer and/or at least one stirring process are feasible. The conductive paste may be applied via at least one dosing needle. However, other methods may be feasible.

Further, the method may comprise at least one drying step, wherein the conductive paste is dried at least to a large extent. Thereby, the electrical contact material may be formed. The drying step may be conducted in a drying cabinet. Exemplarily, the insulation layer may be dried at a temperature of 50° C. to 100° C., preferably of 70° C. to 90° C., more preferably of 80° C. Further, the insulation layer may be dried for 10 h to 48 h, preferably for 20 h to 36 h, more preferably for 24 h.

The method specifically may be performed such that, wherein, in steps b) and c), the electrical contact is arranged such that it extends over at least one edge of the insulation layer.

Additionally or alternatively, as discussed above, the method specifically may be performed such that in step b), the electrical contact is arranged such that it forms a layer, such as a layer of conductive paste or a layer made by applying a conductive paste, e.g., onto the support, specifically a flat support. In step c), the first part may be brought into contact with the layer such that the second conductive layer electrically contacts the layer. The layer specifically may laterally extend over the insulation layer. Thus, as an example, in a top view onto a first side of the insulating layer having the first conductive layer thereon, at least one part of the layer formed by the electrical contact may be visible, protruding from underneath the insulating layer.

This setup, with, in said top view, both the first conductive layer and the part of the layer protruding from underneath the insulation layer being visible, both the first conductive layer and the part of the layer protruding from underneath the insulation layer may be contacted electrically by the electrical connector, even though these elements may be in different depths in a cross-sectional view perpendicular through the insulation layer.

Thus, the at least one electrical connector of the second part may comprise a first electrical connector. Step e) may comprise electrically contacting the first conductive layer with the first electrical connector. Further, the at least one electrical connector of the second part may comprise a second electrical connector. Step e) may comprise electrically contacting the second conductive layer with the second electrical connector via a part of the layer extending laterally over the insulation layer.

The layer of the electrical contact, as discussed, may be formed by coating electrically conductive paste onto at least one support. The at least one support, as an example, may also be part of the medical device, such as of a holder or plug interconnecting an analyte sensor with the medical device. As an example, the support may fully or partially be made of an insulating material.

The proposed methods and devices provide many advantages over known devices and methods. Commonly, vias, specifically micro-vias may be applied. This may lead to a large number of manufacturing steps. Further, common medical devices may comprise copper. Specifically, the vias may be made of or may comprise copper. However, elements comprising copper may present a hazard for the user or the patient. On the contrary, the medical device according to this disclosure comprises the electrical contact. The electrical contact may be provided and/or may be applied to the insulation layer comprising the insulation layer, the first conductive layer and the second conductive layer, as a conductive paste. The electrical contact may allow a double-sided contacting of the interconnect device, specifically of the printed circuit board. The conductive paste may enable a provision of an electric contact on an upper side of the interconnect device, specifically of the printed circuit board, with a micro-via free contaction of a bottom side located conductive layer. The electrical contact material may be copper-free. Further, the interconnect device, e.g., elements of the interconnect device, may be copper-free. This may reduce the hazard for the user or the patient. Further, a number of production steps may be reduced. This may lead to decreased production costs and may decrease the production time.

Summarizing the findings of this disclosure, the following embodiments are preferred:

Embodiment 1

A medical device, wherein the medical device comprises:
at least one first part, wherein the first part comprises at least one interconnect device, wherein the interconnect device comprises:
at least one first conductive layer;
at least one insulation layer; and
at least one second conductive layer, wherein the second conductive layer is separated from the first conductive layer at least by the insulation layer;
at least one electrical contact, wherein the electrical contact comprises at least one electrical contact material, wherein the electrical contact is electrically connected to the second conductive layer, wherein the electrical contact is contactable from one side of the interconnect device opposing the second conductive layer, wherein the electric contact is provided micro-via free; and
at least one second part, wherein the second part comprises at least one electrical connector, wherein the second part is configured to mate with the first part and to establish an electrical connection between the electrical connector of the second part and the first conductive layer and to establish an electrical connection between the electrical connector and the second conductive layer via the electrical contact.

Embodiment 2

The medical device according to the preceding embodiment, wherein the electrical contact material comprises an electrically conductive paste or is applicable to the interconnect device as an electrically conductive paste.

Embodiment 3

The medical device according to the preceding embodiment, wherein the electrically conductive paste comprises at least one of a solution and a dispersion of the electrical contact material.

Embodiment 4

The medical device according to any one of the preceding embodiments, wherein the electrical contact material is copper-free.

Embodiment 5

The medical device according to any one of the preceding embodiments, wherein the electrical contact material comprises at least one material selected from the group consisting of: silver, silver chloride and carbon.

Embodiment 6

The medical device according to any one of the preceding embodiments, wherein the electrical contact material has an electric conductivity of at least 0.1 S/cm, preferably of at least 1.0 S/cm and most preferably of at least 100 S/cm.

Embodiment 7

The medical device according to any one of the preceding embodiments, wherein the electrical contact material is in direct contact with at least one surface of the second conductive layer.

Embodiment 8

The medical device according to any one of the preceding embodiments, wherein the interconnect device has at least one edge, wherein the electrical contact material extends over the edge of the interconnect device.

Embodiment 9

The medical device according to the preceding embodiment, wherein the first conductive layer is located on a first insulation layer side of the insulation layer, wherein the second conductive layer is located on a second insulation layer side of the insulation layer, the second insulation layer side opposing the first side.

Embodiment 10

The medical device according to the preceding embodiment, wherein the electrical contact and the first conductive layer both are at least partially located on the first insulation layer side.

Embodiment 11

The medical device according to any one of the preceding embodiments, wherein the electrical contact material is at least partially located on at least one insulation layer surface of the insulation layer.

Embodiment 12

The medical device according to the preceding embodiment, wherein the insulation layer surface comprises at least one first insulation layer surface, at least one second insulation layer surface and at least one third insulation layer surface, wherein the first insulation layer surface and the second insulation layer surface extend along a direction of extension of the interconnect device, wherein the third insulation layer surface extends along a direction perpendicular to the direction of extension of the interconnect device.

Embodiment 13

The medical device according to the preceding embodiment, wherein the electrical contact material covers the third insulation layer surface at least partially.

Embodiment 14

The medical device according to any one of the two preceding embodiments, wherein the second conductive layer covers the second insulation layer surface at least partially.

Embodiment 15

The medical device according to any one of the three preceding embodiments, wherein the second conductive layer is fitted flush to the insulation layer on at least one edge of the interconnect device.

Embodiment 16

The medical device according to any one of the four preceding embodiments, wherein the second conductive layer forms at least one perpendicular second conductive layer surface which is oriented perpendicular to the direction of extension of the interconnect device.

Embodiment 17

The medical device according to the preceding embodiment, wherein the second conductive layer surface is fitted flush to the third insulation layer surface.

Embodiment 18

The medical device according to any one of the two preceding embodiments, wherein the electrical contact material covers the perpendicular second conductive layer surface at least partially.

Embodiment 19

The medical device according to any one of the seven preceding embodiments, wherein the first conductive layer covers the first insulation layer surface at least partially.

Embodiment 20

The medical device according to any one of the eight preceding embodiments, wherein the electrical contact material covers the first insulation layer surface at least partially.

Embodiment 21

The medical device according to the preceding embodiment, wherein the first conductive layer and the electrical contact material are oriented relative to each other, such that a gap is formed on the first insulation layer surface.

Embodiment 22

The medical device according to the preceding embodiment, wherein the gap is formed at least by the first insulation layer surface, at least one first conductive layer surface which is oriented perpendicular to the direction of extension of the interconnect device, and at least one electrical contact material surface of the electrical contact material which is oriented perpendicular to the direction of extension of the interconnect device.

Embodiment 23

The medical device according to the preceding embodiment, wherein the electrical contact material surface and the first conductive layer surface are essentially parallel to each other.

Embodiment 24

The medical device according to any one of the two preceding embodiments, wherein the gap has a rectangular shape, specifically a square shape.

Embodiment 25

The medical device according to any one of the preceding embodiments, wherein the first conductive layer is at least partially located on the first insulation layer surface, wherein the electrical contact material is partially located on the first insulation layer surface.

Embodiment 26

The medical device according to any one of the preceding embodiments, wherein the electrical contact forms a layer, wherein the first part is in contact with the layer such that the second conductive layer electrically contacts the layer, wherein the layer laterally extends over the first part, wherein the electrical connector of the second part comprises at least one first electrical connector contacting the first conductive layer and wherein the electrical connector further comprises at least one second electrical connector contacting the second conductive layer via a part of the layer of the electrical contact extending laterally over the first part.

Embodiment 27

The medical device according to the preceding embodiment, wherein the electrical connector of the second part comprises a plug, with the at least one first electrical connector and the at least one second electrical connector being part of the plug and being located next to each other, wherein the first electrical connector and the second electrical connector electrically contact the first part from the same side.

Embodiment 28

The medical device according to any one of the two preceding embodiments, specifically not in conjunction with the additional features of embodiments 9 or 10, wherein the medical device comprises the following setup, in the given order:
the layer of the electrical contact,
the second conductive layer being in electrical contact with the layer of the electrical contact,
the insulation layer,
the first conductive layer.

Embodiment 29

The medical device according to any one of the preceding embodiments, wherein the interconnect device is a copper-free interconnect device.

Embodiment 30

The medical device according to any one of the preceding embodiments, wherein the interconnect device is a circuit board, preferably a printed circuit board.

Embodiment 31

The medical device according to any one of the preceding embodiments, wherein the interconnect device is a flexible interconnect device.

Embodiment 32

The medical device according to any one of the preceding embodiments, wherein the first conductive layer and/or the second conductive layer have a thickness of 50 nm to 4 µm, preferably of 100 nm to 3 µm, more preferably of 200 nm to 2 µm.

Embodiment 33

The medical device according to any one of the preceding embodiments, wherein the first conductive layer and/or the second conductive layer comprise at least one material selected from the group consisting of: gold and carbon.

Embodiment 34

The medical device according to any one of the preceding embodiments, wherein the first conductive layer and/or the second conductive layer have an electrical resistance of 0.5 Ohm to 10 Ohm.

Embodiment 35

The medical device according to any one of the preceding embodiments, wherein the insulation layer is an insulating carrier material layer.

Embodiment 36

The medical device according to any one of the preceding embodiments, wherein the insulation layer forms a substrate for at least one of the first conductive layer, the second conductive layer.

Embodiment 37

The medical device according to any one of the preceding embodiments, wherein the insulation layer comprises at least one material selected from the group consisting of: a solder mask; a flexible solder mask; a varnish; an acrylic varnish, in particular NPR-80 and/or ID100; a two-component acrylic varnish; a hardener, in particular PF10/ID36.

Embodiment 38

The medical device according to any one of the preceding embodiments, wherein the insulation layer has a thickness of 15 µm to 30 µm.

Embodiment 39

The medical device according to any one of the preceding embodiments, wherein the first part is a sensor unit, wherein the second part is a sensor electronic unit, specifically an evaluation unit.

Embodiment 40

The medical device according to the preceding embodiment, wherein the sensor unit comprises at least one implantable sensor unit, wherein the implantable sensor unit comprises at least one implantable portion configured for implantation into a body tissue of a user.

Embodiment 41

The medical device according to the preceding embodiment, wherein the medical device is configured for monitoring at least one body function of the user.

Embodiment 42

The medical device according to any one of the two preceding embodiments, wherein the sensor unit comprises at least two sensor electrodes, wherein the at least two sensor electrodes are configured for electrochemically determining at least one concentration of an analyte in the body tissue of the user.

Embodiment 43

The medical device according to any one of the preceding embodiments, wherein the electrical connector of the second part and the electrical contact overlap in an overlap area of 1 $mm^2$ to 50 $mm^2$, preferably of 5 $mm^2$ to 20 $mm^2$ and most preferably in an overlap area of 15 $mm^2$.

Embodiment 44

The medical device according to any one of the preceding embodiments, wherein the interconnect device comprises at least one further layer.

Embodiment 45

A method for manufacturing a medical device, specifically a medical device according to any one of the preceding embodiments, wherein the method comprises the following steps:
a) providing at least one first part of the medical device, by providing at least one insulation layer having at least one first conductive layer and at least one second conductive layer disposed thereon, wherein the second conductive layer is separated from the first conductive layer at least by the insulation layer;
b) providing at least one electrical contact, wherein the electrical contact comprises at least one electrical contact material, specifically at least one electrically conductive paste or at least one light electrically conductive paste, wherein the electrical contact is arranged such that it is contactable from a side of the first part opposing the second conductive layer, wherein the electrical contact is provided micro-via free;
c) electrically connecting the electrical contact to the second conductive layer;
d) providing at least one second part of the medical device, the second part having at least one electrical connector; and
e) mating the second part with the first part and establishing an electrical connection between the electrical connector of the second part and the first conductive layer and establishing an electrical connection between the electrical connector and the second conductive layer via and the electrical contact.

Embodiment 46

The method according to the preceding embodiment, wherein the electrical contact material, specifically a conductive paste, is brought in direct contact with the second conductive layer.

Embodiment 47

The method according to the preceding embodiment, wherein the electrical contact material is placed on the insulation layer such that the conductive paste covers the insulation layer partially.

Embodiment 48

The method according to any one of the two preceding embodiments, wherein the electrical contact material is placed on a part of the insulation layer such that the electrical contact material and the first conductive layer are oriented relative to each other such that a gap between the first conductive layer and the conductive paste emerges.

Embodiment 49

The method according to any one of the three preceding embodiments, wherein the electrical contact material is placed on the part of the insulation layer such that the electrical contact material covers at least one edge of the insulation layer at least partially.

Embodiment 50

The method according to any one of the four preceding embodiments, wherein the electrical contact material is placed on the part of the insulation layer such that the electrical contact material covers the insulation layer at least partially and such that the electrical contact material covers the second conductive layer at least partially, preferably at least one second conductive layer surface of the second conductive layer which extends perpendicular to a direction of extension of the insulation layer.

Embodiment 51

The method according to any one of the preceding method embodiments, wherein the electrical contact material, specifically the conductive paste, comprises at least one material selected from the group consisting of silver, silver chloride and carbon, wherein the material is dispersed in at least one solvent, preferably at least one organic solvent.

Embodiment 52

The method according to the preceding embodiment, wherein the solvent is selected from the group consisting of: diethylene glycol monobutyl ether.

Embodiment 53

The method according to any one of the preceding method embodiments, wherein the conductive paste is centrifuged, preferably vacuum centrifuged, before the conductive material is applied to the interconnect device.

Embodiment 54

The method according to any one of the preceding method embodiments, wherein the conductive paste is applied via at least one dosing needle.

Embodiment 55

The method according to any one of the preceding method embodiments, wherein, in steps b) and c), the electrical contact is arranged such that it extends over at least one edge of the insulation layer.

Embodiment 56

The method according to any one of the preceding method embodiments, wherein, in step b), the electrical contact is arranged such that it forms a layer, wherein, in step c), the first part is brought into contact with the layer such that the second conductive layer electrically contacts the layer, wherein the layer extends laterally over the insulation layer.

Embodiment 57

The method according to the preceding embodiments, wherein the at least one electrical connector of the second part comprises a first electrical connector, wherein step e) comprises electrically contacting the first conductive layer with the first electrical connector, wherein the at least one electrical connector of the second part further comprises a second electrical connector, wherein step e) comprises electrically contacting the second conductive layer with the second electrical connector via a part of the layer extending laterally over the insulation layer.

Embodiment 58

The method according to any one of the two preceding embodiments, wherein the layer of the electrical contact is formed by coating electrically conductive paste onto at least one support, specifically onto at least one electrically insulating support.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
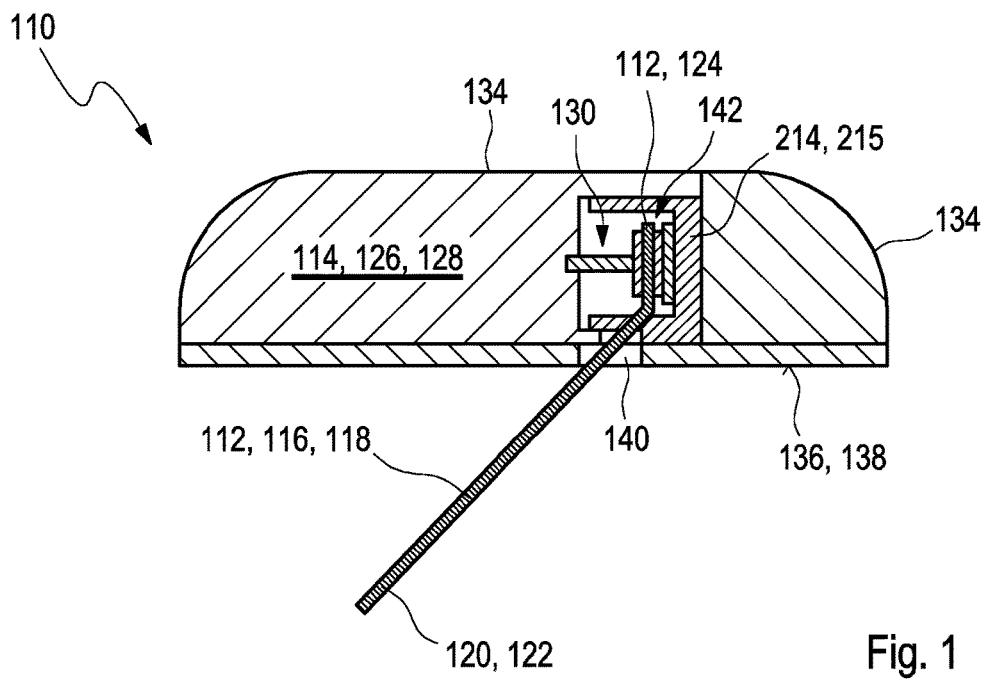
FIG. 1 shows an exemplary embodiment of a medical device in a cross-sectional view.

FIG. 1 shows an exemplary embodiment of a medical device 110 in a cross-sectional view. The medical device 110 comprises at least one first part 112 and at least one second part 114.

Exemplarily, the first part 112 of the medical device 110 may be a sensor unit (or "sensor") 116. The sensor unit 116 may specifically be a transcutaneous sensor unit 118 configured for insertion into a body tissue of a user or a patient. Therefore, the sensor unit 116 may comprise at least one in vivo distal end 120 which may also be referred to as implantable portion 122, and at least one ex vivo proximal end 124. The ex vivo proximal end 124 may be configured to stay outside of the body tissue.

The second part 114 may be a sensor electronic unit 126 (also referred to as "sensor electronics" or "electronics assembly"), specifically an evaluation unit 128. The sensor electronic unit 126 may be adapted for processing data such as for acquiring measurement values and, optionally, for fully or partially evaluating the measurement values. The second part 114 comprises at least one electrical connector 130, preferably a plurality of electrical connectors 130. The second part 114 is configured to mate with the first part 112 and to establish an electrical connection between the electrical connector 130 of the second part 114 and the first conductive layer 146 of the first part 112, and to further establish an electrical connection between the electrical connector 130 and the second conductive layer 150 of the first part 112 via the electrical contact 132, as will be explained in further detail below.

The second part 114 and at least parts of the first part 112, specifically the ex vivo proximal end 124 may be received in at least one housing 134. The housing 134 may comprise at least one flat surface 136 configured for attachment to a skin site of the user or the patient. Therefore, the flat surface may specifically be an adhesive surface 138. The housing 134 may further have at least one through hole 140 for the sensor unit 116.

Figure 2:
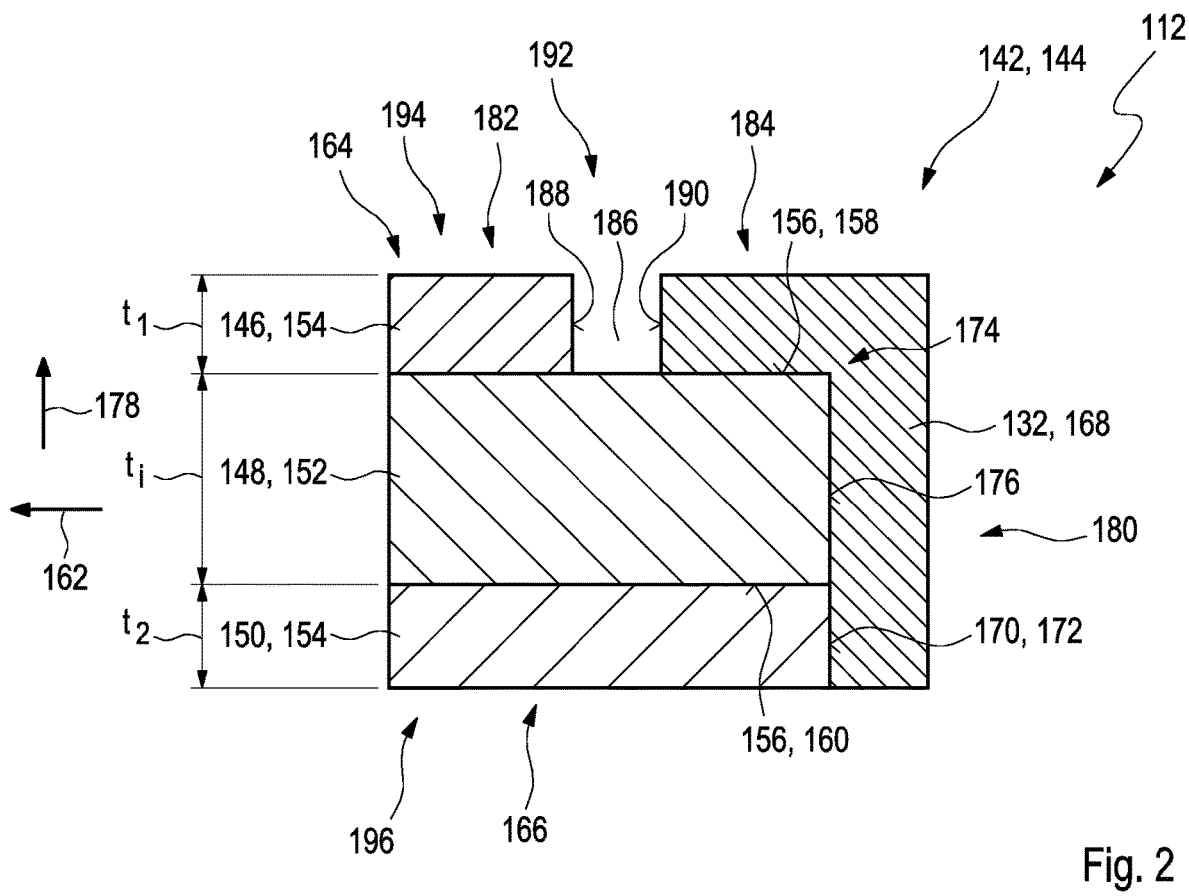
FIG. 2 shows a first exemplary embodiment of a first part and the electrical contact in a cross-sectional view, with the electrical contact reaching over an edge.

FIG. 2 shows a first exemplary embodiment of the first part 112 in a cross-sectional view. The first part 112 may correspond at least partially to the first part 112 according to FIG. 1. Thus, reference may be made to the description of FIG. 1 above. It shall be noted that in this first exemplary embodiment, the electrical connection takes place over an edge. An alternative concept will be explained in further detail below, with respect and with reference to FIGS. 3A to 4C.

The first part 112 comprises at least one interconnect device 142, specifically at least one printed circuit board 144. The interconnect device 142 may specifically be copper-free. The interconnect device 142 comprises at least one first conductive layer 146, at least one insulation layer 148, at least one second conductive layer 150. Further, for contacting purposes, the setup shown in FIG. 2 comprises an electrical contact 132 (also referred to herein as an electrical contact bridge), the function of which will be explained in further detail below.

The insulation layer 148 may be made of at least one insulating carrier material layer 152 which may be configured to mechanically support the first conductive layer 146, the second conductive layer 150 and, optionally, the electrical contact 132. The insulation layer 146 may fully or partially be made of an electrically insulating material and may, as an example, have a thickness $t_i$ of 15 to 30 µm.

The first conductive layer 146 and the second conductive layer 150, as an example, may be or may comprise contact pads, disposed on opposing sides of the insulation layer 146. The situation specifically may owe current in case the sensor unit 116, in the in vivo distal end 120 and/or the implantable portion 122, comprises electrodes such as a working electrode and at least one further electrode (not shown in FIG. 1) on opposing sides of the sensor unit 116. In this case, as an example via conductive traces, at least one first electrode may be contacted via the first conductive layer 146, and at least one second electrode located on an opposing side of the sensor unit 116 may be contacted via the second conductive layer 150. In the setup shown in FIG. 2, an electrical contacting of both the first conductive layer 146 and the second conductive layer 150, by the electrical connector 130, may take place from the upper side, i.e., from the side of the insulation layer 148 with the first conductive layer 146 disposed thereon, i.e., from the same side. As discussed above, the concept shown in FIG. 2 is one alternative implementing the over-the-edge contacting of the second conductive layer 150.

The first conductive layer 146 and the second conductive layer 150 may be applied onto the insulation layer 148 such that at least one coating 154 is formed on at least one surface 156 of the insulation layer. The second conductive layer 150 is separated from the first conductive layer 146 at least by the insulation layer 148. The insulation layer 148 may specifically comprise at least one first insulation layer surface 158 and at least one second insulation layer surface 160, wherein the first insulation layer surface 158 and the second insulation layer surface 160 may extend along a direction of extension 162 of the interconnect device 142. The first insulation layer surface 158 may be located on a first insulation layer side 164 of the insulation layer 148 and the second insulation layer surface 160 may be located on a second insulation layer side 166 of the insulation layer 148. Thus, the insulation layer 148 may be located between the first conductive layer 146 and the second conductive layer 150. The first conductive layer 146 may have a thickness $t_i$ of 50 nm to 4 µm and the second conductive layer 150 may have a thickness $t_2$ of 50 nm to 4 µm.

The electrical contact 132 is provided micro-via free. The electrical contact 132 comprises at least one electrical contact material 168. Exemplarily, the electrical contact material 168 may comprise at least one of silver, silver chloride and carbon. However, other embodiments may be feasible. Specifically, the electrical contact material 168 comprises an electrically conductive paste or is applicable to the interconnect device 142 as an electrically conductive paste.

The electrical contact 132 is electrically connected to the second conductive layer 150. Specifically, the electrical contact material 168 may be in direct contact with at least one surface 170 of the second conductive layer 150 and may even overlap with the second conductive layer 150. Specifically, the surface 170 may be a perpendicular second conductive layer surface 172 being oriented transverse, specifically perpendicular, to the direction of extension 162.

Further, the interconnect device may have at least one edge or corner 174 and the electrical contact material 168 may extend over the edge 174 of the interconnect device 142. By extending over the at least one edge 174, the second conductive layer 150 may be contacted, via the electrical contact 132, from the same side as the first conductive layer 146, even though these conductive layers 146, 150 are generally disposed on opposing sides, without the necessity of providing vias within the insulation layer 148. Thus, from a manufacturing perspective, vias are generally difficult to produce and require additional manufacturing steps.

Specifically, the second conductive layer 150 may be located on the second insulation layer side 166 of the insulation layer 148, the second insulation layer side 166 opposing the first insulation layer side 164. The electrical contact 132 and the first conductive layer 146 both may be at least partially located on the first insulation layer side 164.

Further, the electrical contact material 168 may be at least partially located on at least one insulation layer surface 156 of the insulation layer 148. Specifically, the insulation layer surface 156 may comprise the first insulation layer surface 158 and the second insulation layer surface 160. The first insulation layer surface 158 and the second insulation layer surface 160 may extend along the direction of extension 162 of the interconnect device 142. The first conductive layer 146 may cover the first insulation layer surface 158 at least partially. Further, the second conductive layer 150 may cover the second insulation layer surface 160 at least partially. Further, the insulation layer 148 may comprise at least one third insulation layer surface 176. The third insulation layer surface 176 may extend along a direction 178 transverse, specifically perpendicular, to the direction of extension 162 of the interconnect device 142. Specifically, the third insulation layer surface 176 may refer to a narrow side 180 of the insulation layer 148.

The second conductive layer 150 may cover the second insulation layer surface 160 at least partially. Specifically, the second conductive layer 150 may be fitted flush to the insulation layer 148. Specifically, the perpendicular second conductive layer surface 172 may be fitted flush to the third insulation layer surface 176. The perpendicular second conductive layer surface 172 and the third insulation layer surface 178 may form the narrow side 180 of the interconnect device 142. Specifically, the electrical contact material 168 may cover the perpendicular second conductive layer surface 172 at least partially.

Moreover, the electrical contact material 168 may cover the first insulation layer surface 158 at least partially. The first conductive layer 146 and the electrical contact material 168 may both cover the first insulation layer surface 158. Specifically, the first conductive layer 146 may cover a first section 182 of the first insulation layer surface 158 and the electrical contact material 168 may cover a second section 184 of the first insulation layer surface 158. The first section 182 and the second section 184 may specifically be distinct from each other. Specifically, the first conductive layer 146 and the electrical contact material 168 may be oriented relative to each other, such that a gap 186 is formed on the first insulation layer surface 158. The gap 186 may be formed at least by the first insulation layer surface 156, at least one first conductive layer surface 188 which is oriented transverse, specifically perpendicular, to the direction of extension 168 of the interconnect device 142, and at least one electrical contact material surface 190 of the electrical contact material 168 which is oriented transverse, specifically perpendicular, to the direction of extension 162 of the interconnect device 142. The electrical contact material surface 190 and the first conductive layer surface 188 may be parallel to each other. The gap 186 may have a rectangular shape, specifically a square shape.

The electrical contact 132 is contactable from one side 192 of the interconnect device 142 opposing the second conductive layer 150. Particularly, the electrical contact 132 may be contactable from one side 192 of the interconnect device 142 opposing the second conductive layer 150 relative to the insulation layer 148. Specifically, the interconnect device 142 may comprise at least one first interconnect device side 194 which is at least partially covered by first conductive layer 146 and at least one second interconnect device side 196 which is at least partially covered by the second conductive material 150. Thus, the electrical contact 132 may be contactable from the first interconnect device side 194.

Figure 3:
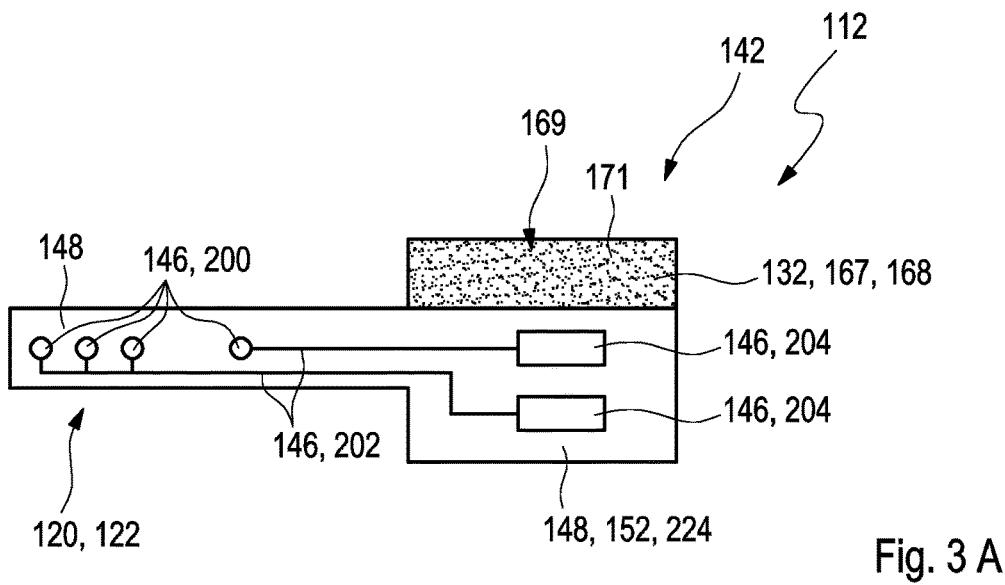
FIGS. 3A to 3C show a second exemplary embodiment of a first part and an electrical contact, with the electrical contact forming a plane layer underneath the first part, in a top view (FIG. 3A) and in a cross-sectional view (FIG. 3B) as well as of an insulation layer of the first part in a bottom view (FIG. 3C)
Figure 3:
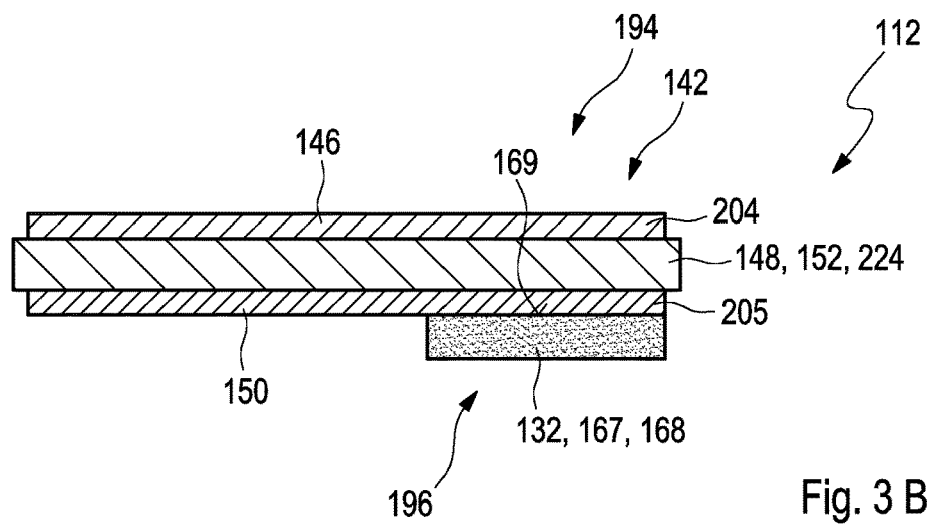
Figure 3:
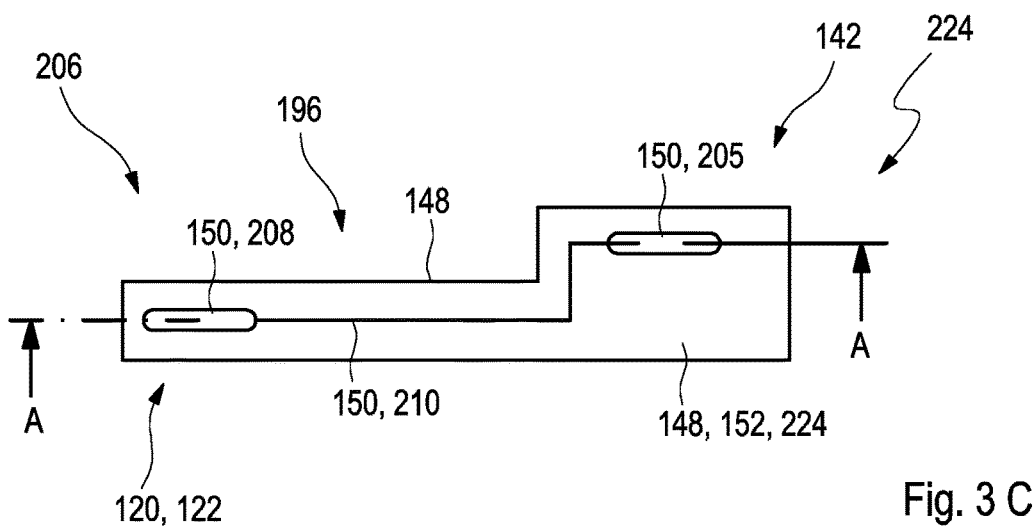
Figure 4:
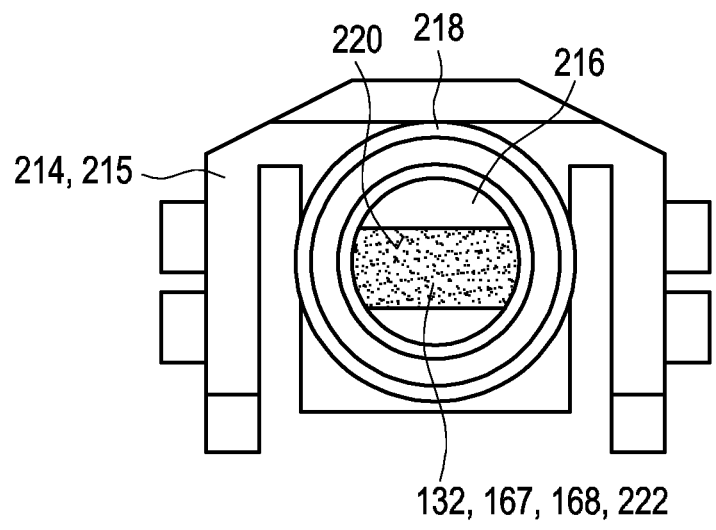
FIGS. 4A to 4C show an exemplary method for manufacturing a medical device.
Figure 4:
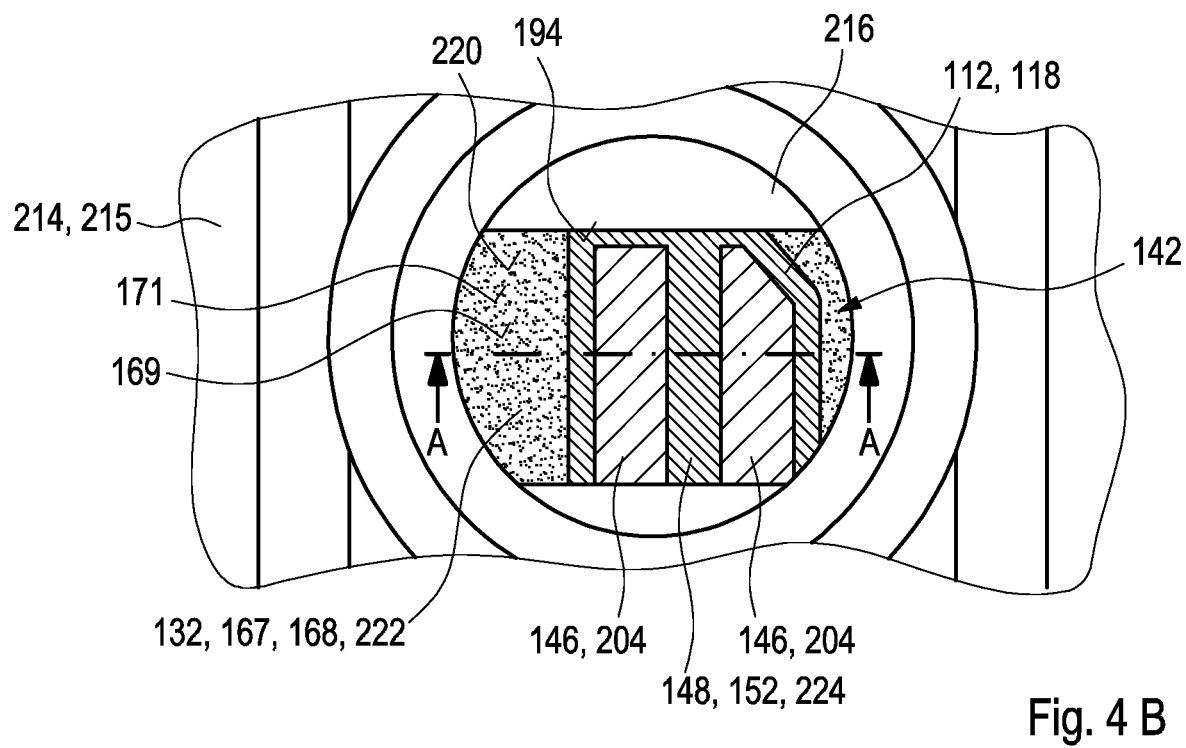
Figure 4:
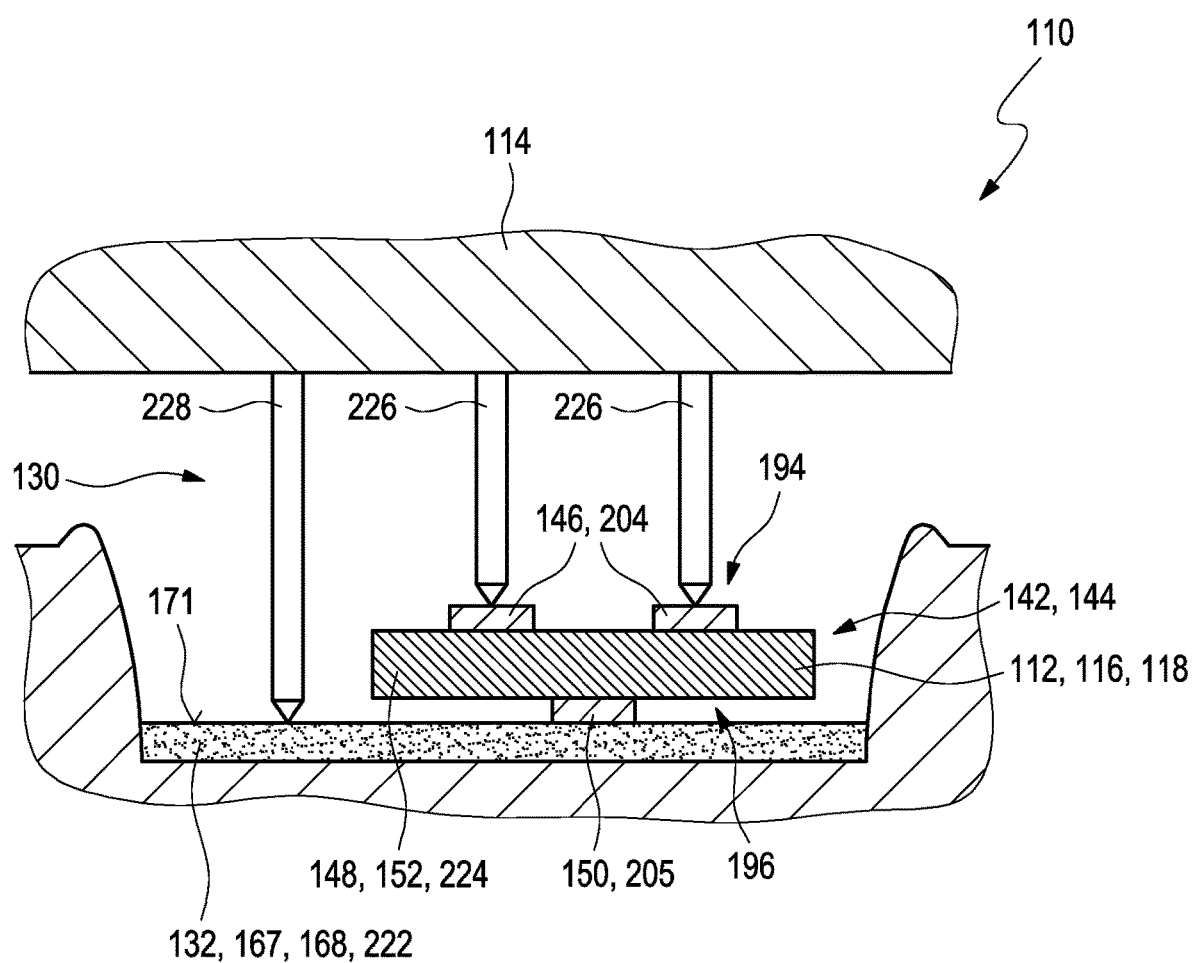

The concept of extending the electrical contact 132 over at least one edge 174 of the insulation layer 148 is one potential concept for contacting both the first conductive layer 146 and the second conductive layer 150 from the same side, without providing a via within the insulation layer 148. FIGS. 3A to 4C show an alternative concept in which, even though located in different depths of a layer setup, the first and second conductive layers 146, 150 may be contacted via an electrical contact 132, with the electrical contact 132 forming a layer 167, extending laterally over the insulation layer 148. Therein, FIGS. 3A to 3C show an exemplary setup of the first part 112 and the electrical contact 132, FIGS. 4A and 4B show an implementation of the first part 112 and the electrical contact 132 into a connector element 214 forming a support 215, and FIG. 4B shows a contacting of the setup of FIG. 4B by the electrical connector 130, as also shown in FIG. 1. FIGS. 4A to 4C may also be used as an illustration of an exemplary embodiment for manufacturing the medical device 110, specifically for interconnecting the first part 112 and the second part 114.

Thus, FIG. 3A shows a second exemplary embodiment of a first part 112, e.g., of the sensor unit 116, in a top view, FIG. 3B shows the first part 112 in a cross-sectional view and FIG. 3C shows a substrate 224 of the first part 112, formed by the insulation layer 148, in a bottom view. The first part 112 specifically may correspond to the first part 112 according to FIG. 1.

In FIG. 3A, a top view of the first part 112 is illustrated and in FIG. 3B a cross-sectional view of the first part 112 is shown. As discussed above in the context of FIG. 2, the sensor unit 116 may comprise electrodes on opposing sides of the insulation layer 148, specifically in the in vivo distal end 120 and/or the implantable portion 122. These electrodes, in FIGS. 3A and 3C, are denoted by reference numbers 200 and 208, respectively and may form part of the first conductive layer 146 and the second conductive layer 150, respectively. As an example, electrodes 200, 208 may comprise at least one working electrode and at least one further electrode, e.g., at least one reference electrode and/or at least one counter electrode. These electrodes may be contacted via conductive paths 202, 210, which also form part of the first conductive layer 146 and second conductive layer 150, respectively, disposed on a first side or first interconnect device side 194 of the insulation layer 148, shown in FIG. 3A, and on a second side or second interconnect device side 196 of the insulation layer 148, shown in FIG. 3C. The conductive paths 202, 210 may lead to contact pads 204, 205, disposed on the opposing first and second interconnect device sides 194, 196, respectively. These contact pads 204, 205 also form part of the first and second conductive layers 146, 150, respectively.

In order to electrically contact both the first conductive layer 146 and the second conductive layer 150 from the same side, i.e., from the first interconnect device side 194, the electrical contact 132 is provided. In this embodiment, the electrical contact 132 is embodied as a layer 167 formed by an electrical contact material 168. As can be seen in FIG. 3B, the electrical contact material 168 may form at least one electrical contact material surface 169 and the substrate 224 having the first conductive layer 146, the insulation layer 148 and the second conductive layer 150 may be located on top of the electrical contact material surface 169. The insulation layer 148 may form a substrate 224, which may partially cover the electrical contact material surface 169, such that a free area 171 may be provided which is not covered by the substrate 224 and is thus contactable for another element. Thus, the layer 167 extends, laterally, over the insulation layer 148 and, thus, forms a portion or free area 171, which may be contacted from the same side as the first conductive layer 146. Since the layer 167 is in electrical contact with the second conductive layer 150, by contacting the layer 167, an electrical contact may be established with the second conductive layer 150, from the same side as for the first conductive layer 146, i.e., from the first interconnect device side 194, as will be explained in further detail below with respect to FIG. 4C.

In FIG. 3C, a reverse view of the substrate 224 is illustrated. The illustration as depicted in FIG. 3B refers to a sectional view of the illustration according to FIG. 3C which is illustrated with line A-A. Thus, the second interconnect device side 196 may have one or more electrodes 208, one or more conductive paths 210 and one or more contact pads 205, forming part of the second conductive layer 146. Specifically, as shown in FIG. 3B, the at least one contact pad 205 may be in direct contact with the electrical contact material surface 169.

In FIGS. 4A to 4C an exemplary method for manufacturing a medical device 110 is shown, using the second alternative embodiment of FIGS. 3A to 3C. Therein, the first part 112, being embodied as a transcutaneous sensor unit 118, and the electrical contact 132 as shown in FIGS. 3A to 3C is used. Thus, reference may be made to the description of FIGS. 3A to 3C above.

In a first step, as illustrated in FIG. 4A, at least one connector element 214 may be provided, which functions as a support 215. The support 215, as an example and as shown in FIG. 1 above, specifically may be part of a body mount and may be configured for holding the sensor unit 116.

The connector element 214 may be made of at least one thermoplastic polymer such as acrylonitrile butadiene styrene (ABS). The connector element 214 may comprise at least one receptacle 216, e.g., having a round shape. Further, the connector element 214 may comprise at least one sealing ring 218 which surrounds the receptacle 216. Thus, specifically, the connector element 214 may fully or partially be embodied as a watertight plug, which may be made with a corresponding connector of the sensor electronics unit 126, as shown in FIG. 1.

The method firstly comprises providing the at least one electrical contact 132. In this case, this electrical contact 132 is provided by disposing the electrical contact material 168 onto a supporting surface 220 of the receptacle 216. As an example, at least one conductive paste 222 may be placed onto the at least one supporting surface 220 of the receptacle 216. Specifically, the conductive paste may comprise silver, silver chloride and carbon which may be diluted with diEthylene gGlycol monobutyl ether (DEGMBE). The conductive paste 222 may be dosed, e.g., via a dosing needle such as a precision tips 25 GA and a syringe, specifically a 2.5 ml syringe. Thereafter, the conductive paste 222 may be dried in a drying cabinet for 24 h at a temperature of 80° C. and, thus, the electrical contact 132 may be formed.

Thereafter, in a further step, as also illustrated in FIG. 4B, the second part 112 may be provided. Thus, the insulation layer 148 forming the substrate 224 may be provided, as discussed above in the context of FIGS. 3A to 3C, with the second interconnect device side 196 (not visible in this Figure) facing the electrical contact 132. Thus, an electrical connection is formed between the contact pads 204 disposed on the second interconnect device side 196 and the electrical contact 132. Since, as visible in FIG. 4B, the layer 176 laterally protrudes over the substrate 224 and forms the portion of the free area 171, the top view shown in FIG. 4B exhibits three independently contactable portions: firstly, the free area 171, which is electrically connected to the second conductive layer 150 and to the contact pads 205, and, secondly and thirdly, the contact pads 204 which forms part of the first conductive layer 146.

In FIG. 4C, finally, a step of providing at least one second part 114 having the at least one electrical connector 130 as well as a step of making the second part 114 with the first part 112 is shown. This step, as an example, may take place when the sensor electronics unit 126 and/or evaluation unit 128 is put in place in FIG. 1. FIG. 4C shows a cross-sectional view along line A-A in FIG. 4B.

Thus, as shown therein, the electrical connector 130 comprises, in this embodiment with two contact pads 204, two first electrical connectors 226 which, as an example, are embodied as contact pins pressed onto the contact pads 204 of the first conductive layer 146 on the first interconnect device side 194. On the opposing side, the second interconnect device side 196, as outlined above, the contact pad 205 of the second conductive layer 150 is in the electrical contact with the layer 167 of the electrical contact 132. As an example, the contact pins and/or other types of contact of the first electrical connector 226 may be used for pressing the first part 112, with the contact pads 205, onto the layer 167. The electrical connector 130 further comprises at least one second electrical connector 228 which, as an example, may also be embodied as a contact pin. The second electrical connector 228 contacts the layer 167 in the free area 171. Consequently, both the contact pads 204 and the contact pad 205, even though disposed on opposing sides 194, 196, may be contacted from the same side, i.e., from side 194 in this setup. No micro-vias are required. The electrical connector 130, as an example, may also comprise other types of spring contacts. The second electrical connector 228, as an example, may be slightly longer as compared to the first electrical connectors 226, since the distance between the second part 114 and the layer 167 is slightly larger than the distance between the second part 114 and the contact pads 204.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 medical device
112 first part
114 second part
116 sensor unit
118 transcutaneous sensor unit
120 in vivo distal end
122 implantable portion
124 ex vivo proximal end
126 sensor electronic unit
128 evaluation unit
130 electrical connector
132 electrical contact
134 housing
136 flat surface
138 adhesive surface
140 through hole
142 interconnect device
144 printed circuit board
146 first conductive layer
148 insulation layer
150 second conductive layer
152 insulating carrier material layer
154 coating
156 surface
158 first insulation layer surface
160 second insulation layer surface
162 direction of extension
164 first insulation layer side
166 second insulation layer side
167 layer of the electrical contact
168 electrical contact material
169 electrical contact material surface
170 surface
171 free area
172 perpendicular second conductive layer surface
174 edge
176 third insulation layer surface
178 direction
180 narrow side
182 first section
184 second section
186 gap
188 first conductive layer surface
190 electrical contact material surface
192 side
194 first interconnect device side
196 second interconnect device side
200 electrode
202 conductive path
204 contact pad
205 contact pad
208 electrode
210 conductive path
212 sectional view
214 connector element
215 support
216 receptacle
218 sealing ring
220 supporting surface
222 conductive paste
224 substrate
226 first electrical connector
228 second electrical connector

What is claimed is:

1. A medical device, comprising:
a sensor having an interconnect, the interconnect comprising a first conductive layer, an insulation layer, a second conductive layer separated from the first conductive layer by the insulation layer, and an electrical contact, wherein the electrical contact is electrically connected to the second conductive layer, contactable from one side of the interconnect opposing the second conductive layer, and provided micro-via free; and an electronics assembly having an electrical connector, the electronics assembly configured to mate with the interconnect to establish an electrical connection between the electrical connector and the first conductive layer via the electrical contact.

2. The medical device according to claim 1, wherein the electrical contact comprises an electrically conductive paste.

3. The medical device according to claim 1, wherein the electrical contact is copper-free.

4. The medical device according to claim 1, wherein the electrical contact comprises at least one material selected from the group consisting of silver, silver chloride and carbon.

5. The medical device according to claim 1, wherein the interconnect has an edge and the electrical contact extends over the edge.

6. The medical device according to claim 5, wherein:
the first conductive layer is located on a first insulation layer side of the insulation layer;
the second conductive layer is located on a second insulation layer side of the insulation layer, the second insulation layer side opposing the first side; and
the electrical contact and the first conductive layer both are at least partially located on the first insulation layer side.

7. The medical device according to claim 1, wherein:
a portion of the electrical contact extends laterally over the same side of the insulation layer as the first conductive layer; and
the electrical connector has a first connector part contacting the first conductive layer and a second connector part contacting the second conductive layer via the portion of the electrical contact that extends laterally over the same side of the insulation layer as the first conductive layer.

8. The medical device according to claim 7, wherein the electrical connector comprises a plug that includes at least one of the first connector part and the second connector part, wherein the first connector part and the second connector part electrically contact the interconnect from the same side.

9. A method for manufacturing a medical device, comprising:
a) providing an insulation layer;
b) providing a first conductive layer on a first side of the insulation layer and a second conductive layer on a second side of the insulation layer opposite the first side, wherein the second conductive layer is separated from the first conductive layer by the insulation layer;
c) providing an electrical contact that is electrically connected to the second conductive layer; and arranging a contact surface of the electrical contact to face in the same direction as the first conductive layer;
d) providing an electronics assembly with an electrical connector first connector part and a second connector part;
e) establishing a first electrical connection between the first connector part and the first conductive layer; and f) via the electrical contact, establishing a second electrical connection between the second connector part and the second conductive layer.

10. The method according to claim 9, comprising arranging the electrical contact such that it extends over an edge of the insulation layer.

11. The method according to claim 9, wherein, the electrical contact is arranged as a layer that laterally extends over the first side of the insulation layer.

12. The method according to claim 9, wherein the first connector part and the second connector part face in the same direction and face the first conductive layer and face at least part of the electrical contact.

13. The method according to claim 9, wherein the electrical contact is formed by coating electrically conductive paste onto at least one support.

14. A medical device, comprising:
a sensor having a first side facing in a first direction and a second side facing in a second direction opposite the first direction, the sensor further comprising:
an insulative substrate,
a first conductive layer disposed on a first side of the substrate and facing in the first direction,
a second conductive layer disposed on a second side of the substrate opposite the first side and facing in the second direction, and
an electrical contact bridge electrically connected to the second conductive layer, wherein at least a portion of the electrical contact bridge faces in the first direction and is exposed for electrical contact, and
an electronics assembly configured to mate with the sensor to establish an electrical connection, the electronics assembly having an electrical connector that contacts the first conductive layer from the first side of the sensor and also contacts the electrical contact bridge from the first side of the sensor.

15. The medical device according to claim 14, wherein the electrical contact bridge comprises an electrically conductive paste.

16. The medical device according to claim 14, wherein the electrical contact bridge is copper-free.

17. The medical device according to claim 14 wherein the electrical contact bridge comprises at least one material selected from the group consisting of silver, silver chloride and carbon.

18. The medical device according to claim 14, wherein the electrical contact bridge extends over an edge of the substrate and is at least partially disposed on the first side of the substrate and faces in the first direction.

19. The medical device of claim 14, wherein the electrical contact bridge extends laterally beyond an edge of the substrate.

20. The medical device of claim 14, wherein the electrical contact bridge is free of vias.

* * * * *